(12) United States Patent
Urano et al.

(10) Patent No.: US 8,748,795 B2
(45) Date of Patent: Jun. 10, 2014

(54) METHOD FOR INSPECTING PATTERN DEFECT AND DEVICE FOR REALIZING THE SAME

(75) Inventors: Yuta Urano, Yokohama (JP); Hiroyuki Nakano, Yokohama (JP); Shunji Maeda, Yokohama (JP); Sachio Uto, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 308 days.

(21) Appl. No.: 12/329,274

(22) Filed: Dec. 5, 2008

(65) Prior Publication Data

US 2009/0091750 A1  Apr. 9, 2009

Related U.S. Application Data

(62) Division of application No. 11/325,550, filed on Jan. 5, 2006, now Pat. No. 7,465,935.

(30) Foreign Application Priority Data

Jan. 21, 2005  (JP) ................................. 2005-013472

(51) Int. Cl.
  *G01N 21/00*  (2006.01)
(52) U.S. Cl.
  USPC ............. 250/214 VT; 356/237.2; 250/559.45
(58) Field of Classification Search
  USPC ...................... 250/214 VT, 559.45, 310, 372; 356/237.2, 237.3
  See application file for complete search history.

(56) References Cited

U.S. PATENT DOCUMENTS

| 5,046,847 | A | 9/1991 | Nakata et al. |
| 5,337,340 | A | 8/1994 | Hynecek |
| 6,411,377 | B1 | 6/2002 | Noguchi |

(Continued)

FOREIGN PATENT DOCUMENTS

| JP | 62-089336 | 4/1987 |
| JP | 10-510359 A1 | 10/1998 |

(Continued)

OTHER PUBLICATIONS

Japanese Office Action, dated Feb. 1, 2011, issued in corresponding Japanese Patent Application No. 2005-013472.

*Primary Examiner* — Tony Ko
(74) *Attorney, Agent, or Firm* — Antonelli, Terry, Stout & Kraus, LLP.

(57) ABSTRACT

When using a CCD sensor as a photo-detector in a device for inspecting foreign matters and defects, it has a problem of causing electric noise while converting the signal charge, produced inside by photoelectric conversion, into voltage and reading it. Therefore, the weak detected signal obtained by detecting reflected and scattered light from small foreign matters and defects is buried in the electric noise, which has been an obstacle in detecting small foreign matters and defects. In order to solve the above problem, according to the present invention, an electron multiplying CCD sensor is used as a photo-detector. The electron multiplying CCD sensor is capable of enlarging signals brought about by inputted light relatively to the electric noise by multiplying the electrons produced through photoelectric conversion and reading them. Accordingly, compared to a conventional CCD sensor, it can detect weaker light and, therefore, smaller foreign matters and defects.

14 Claims, 19 Drawing Sheets

(56) References Cited

U.S. PATENT DOCUMENTS

| | | |
|---|---|---|
| 6,617,603 B2 * | 9/2003 | Ishiguro et al. .......... 250/559.45 |
| 6,819,416 B2 | 11/2004 | Maeda et al. |
| 6,902,527 B1 | 6/2005 | Doguchi et al. |
| 2002/0080345 A1 * | 6/2002 | Ishiguro .................. 356/237.2 |
| 2002/0088952 A1 * | 7/2002 | Rao et al. ................. 250/559.45 |
| 2002/0168787 A1 | 11/2002 | Noguchi et al. |
| 2004/0106862 A1 * | 6/2004 | Kohama ........................ 600/407 |
| 2005/0185172 A1 | 8/2005 | Ishimaru et al. |

FOREIGN PATENT DOCUMENTS

| | | |
|---|---|---|
| JP | 11-201909 A1 | 7/1999 |
| JP | 11-204072 | 7/1999 |
| JP | 2000-338048 | 12/2000 |
| JP | 2001-005961 | 1/2001 |
| JP | 2001-169193 | 6/2001 |
| JP | 2001-255278 A1 | 9/2001 |
| JP | 2002-181725 | 6/2002 |
| JP | 2004-12275 | 1/2004 |

* cited by examiner

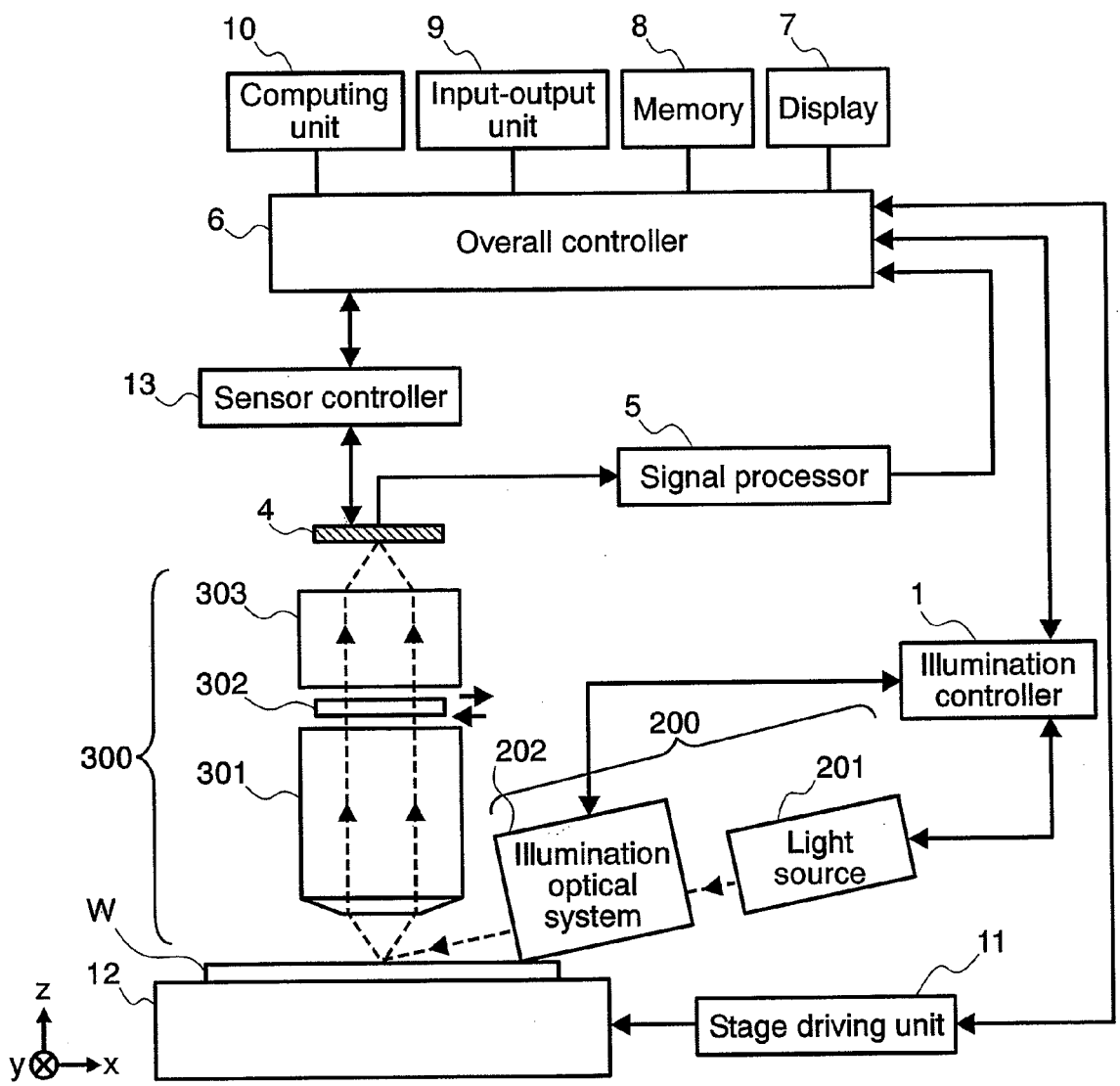
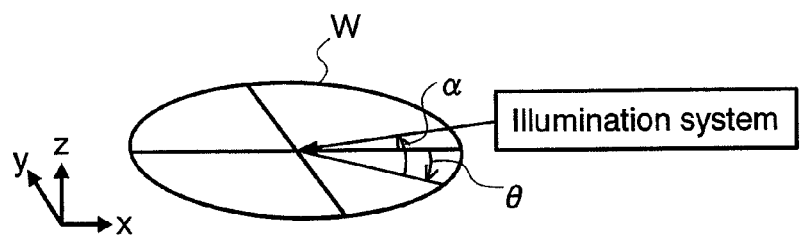

FIG.5
(a)
Outside shape of on-chip
electron multiplying CCD sensor
(b)
Pixel configuration of on-chip
electron multiplying CCD sensor
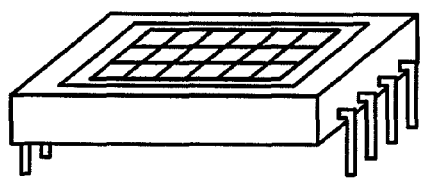
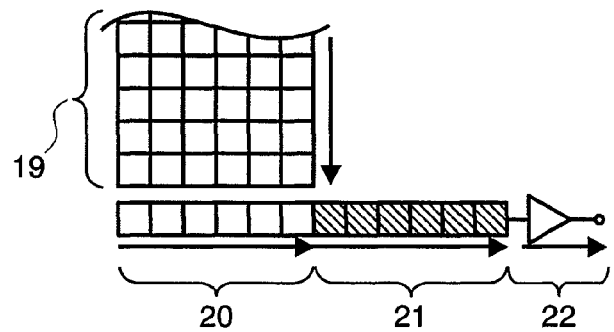
FIG.6
(a)
Electron-bombarded
multiplying CCD sensor
(b)
On-chip electron
multiplying CCD sensor
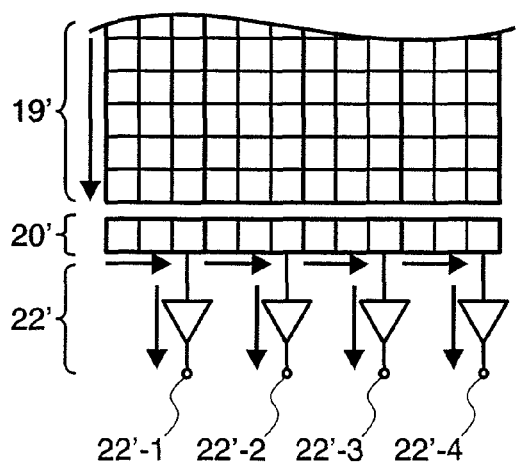
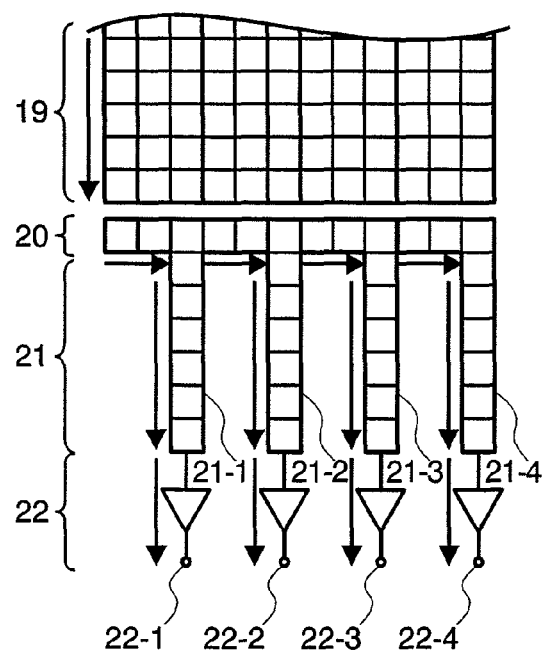

FIG.7
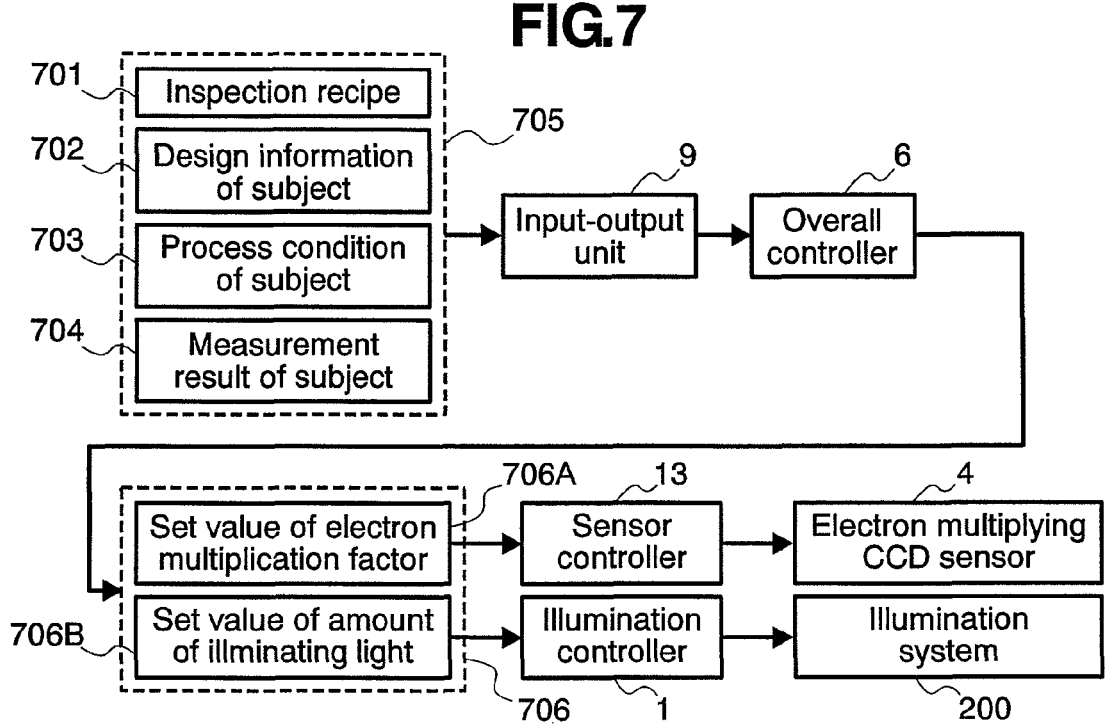
FIG.8
(a)
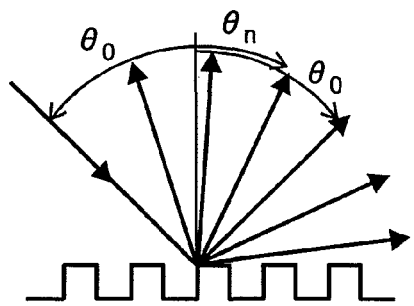
(b)
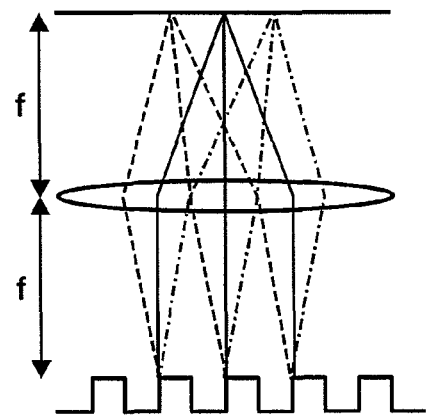
(c)
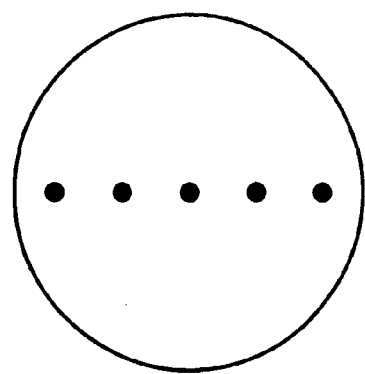
(d)
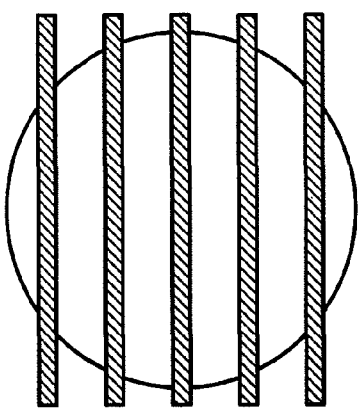

FIG.15
(a)
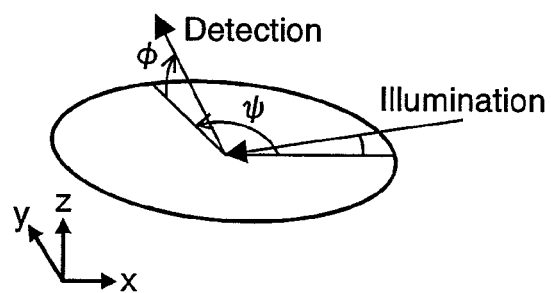
(b)
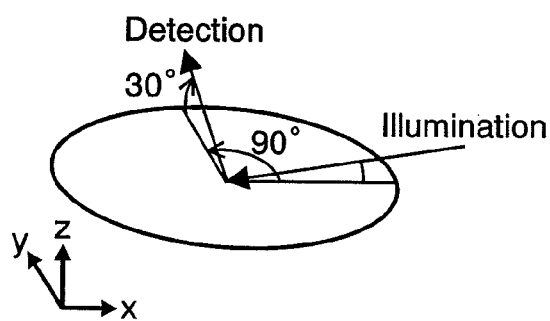
(c)
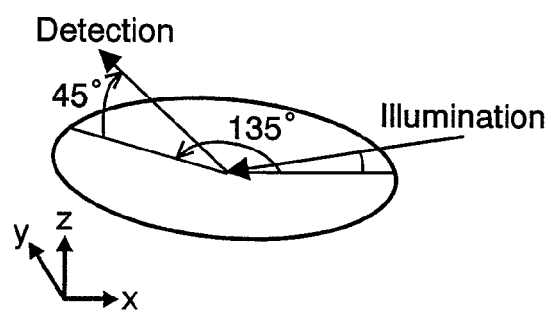

FIG.18
(a)
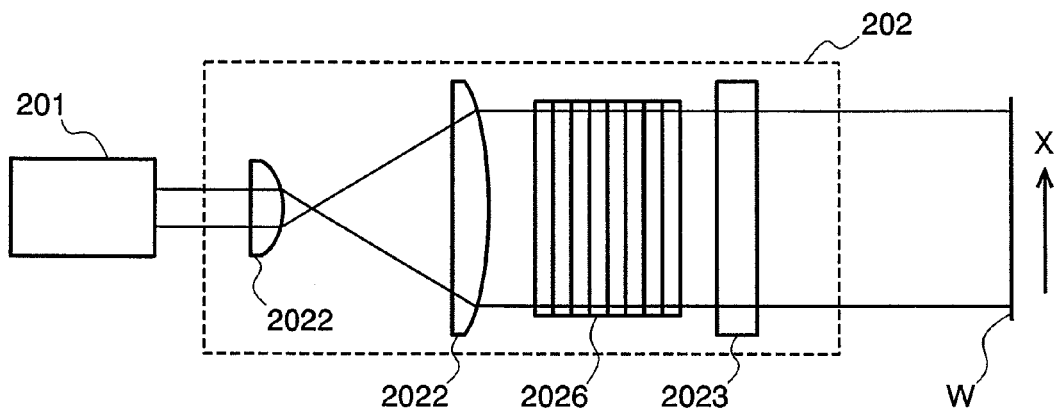
(b)
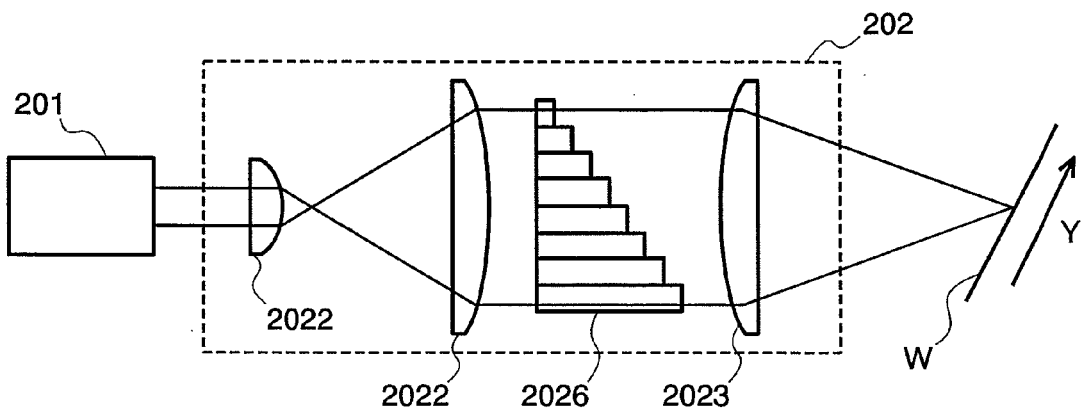
(c)
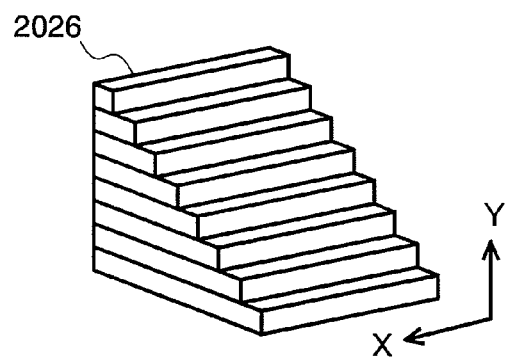

FIG.24
(a)
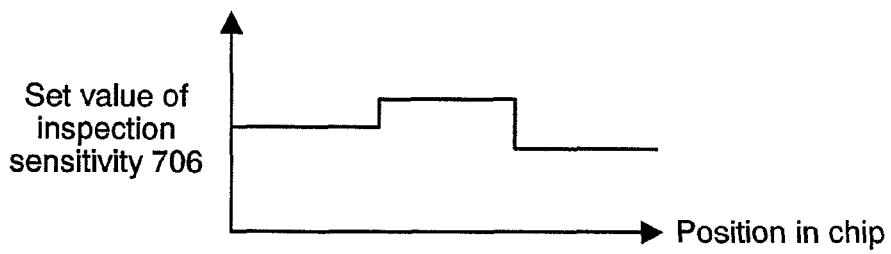
(b)
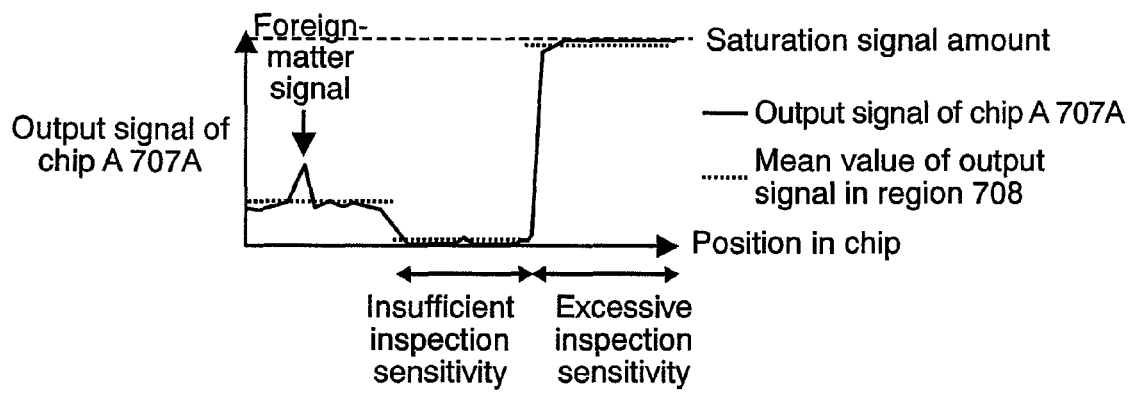
(c)
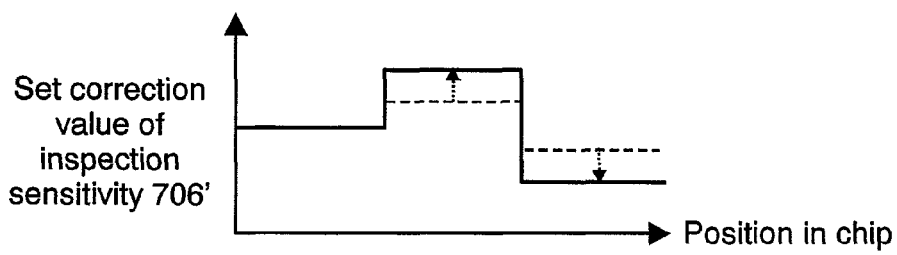
(d)
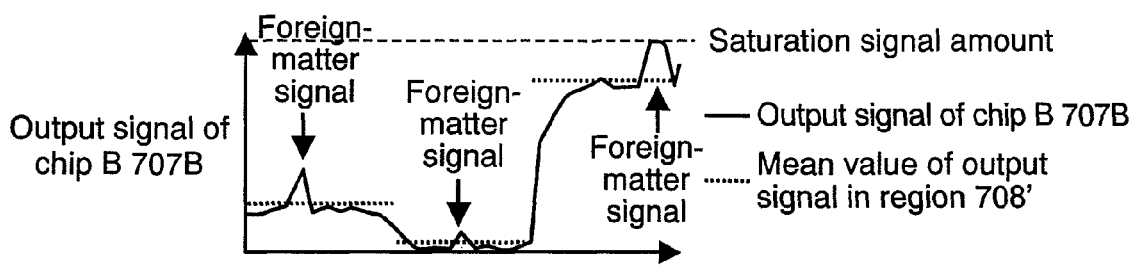

METHOD FOR INSPECTING PATTERN DEFECT AND DEVICE FOR REALIZING THE SAME

CROSS REFERENCE TO RELATED APPLICATION

This application is a divisional application of U.S. application Ser. No. 11/325,550, filed Jan. 5, 2006 now U.S. Pat. No. 7,465,935, the contents of which are incorporated herein by reference.

BACKGROUND OF THE INVENTION

1. Field of the Invention

The present invention relates to a method and device for detecting foreign matters and defects produced in the manufacturing processes of LSIs, liquid crystal substrates, etc. wherein patterns are formed on the substrates.

2. Description of the Related Art

In the past, as disclosed in Japanese Patent Laid-open No. 62-89336, such a method for detecting foreign matters and defects on a semiconductor wafer is known that a laser beam is irradiated on the semiconductor wafer and scattered light from foreign matters is detected when there are such foreign matters on the semiconductor wafer and the foreign matters and defects are inspected by comparing the scattered light with an inspection result of a semiconductor wafer of the same kind inspected in advance.

In the conventional device for inspecting foreign matters and defects, a CCD sensor has been used as a photo-detector. A CCD sensor is capable of imaging more than 1,000 pixels at the same time and reading them at high speed. Therefore, by using it as a detector of the device for inspecting foreign matters and defects, it is possible to shorten the inspection time. However, the CCD sensor has a problem of causing electric noises when converting a signal charge generated inside by photoelectric conversion into voltage and reading it. Therefore, when detecting smaller foreign matters and defects, the weak detected signal gained by detecting reflected and scattered light from those smaller foreign matters and defects may buried in electric noises and the smaller foreign matters and defects cannot be detected.

SUMMARY OF THE INVENTION

In order to solve the above problem, as a photo-detector, it is conceivable to use a photomultiplier tube with a built-in electron multiplying mechanism and being highly sensitive to weak light. However, compared to a CCD sensor, it is difficult to multi-channelize the photomultiplier tube and the number of pixels it can handle at the same time is limited. Therefore, when it is used as a detector for the device of inspecting foreign matters and defects, it takes considerable time for the inspection.

In order to solve the above problems, according to the present invention, an electron multiplying CCD sensor is used as a photo-detector of the device for inspecting foreign matters and defects. The electron multiplying CCD sensor is capable of enlarging signals brought about by inputted light relatively to electric noises by multiplying the electrons produced through photoelectric conversion and reading them afterwards. Therefore, compared to a conventional CCD sensor, it can detect weaker light. Further, like the conventional CCD sensor, it can image more than 1,000 pixels at the same time and read them at high speed. Still further, its electron multiplication factor is variable.

One example of such an electron multiplying CCD sensor having the characteristic described above is an electron-bombarded multiplying CCD sensor disclosed in Japanese Patent Laid-open No. 11-204072 wherein electrons are multiplied by causing electron-bombardment multiplication. Another example is an on-chip electron multiplying CCD sensor disclosed in U.S. Pat. No. 5,337,340 wherein electrons are multiplied by causing impact ionization during the charge transfer.

By using the electron multiplying CCD sensor as a photo-detector of the device for inspecting foreign matters and defects, it becomes possible to perform a highly sensitive inspection with basically the same construction as that of the conventional device and with the same inspection speed.

Further, the subject to be inspected can be scanned at high speed by using a linear motor as a driving means for a stage on which the subject is placed and moved. When the scanning speed is increased, the amount of light to be detected decreases as much as the decrease in accumulating time of the detected light. However, by using a highly-sensitive electron multiplying CCD sensor as a photo-detector, an inspection with the same or higher sensitivity than that of the conventional device and at higher speed can be achieved.

Further, by adjusting the electron multiplication factor of the electron multiplying CCD sensor, it is possible to change sensitivity in inspection. When inputting the same amount of light, compared to the conventional CCD sensor which does not multiply electrons, the electron multiplying CCD sensor produces more signal electrons because it multiplies electrons and is apt to be saturated. When there is considerable amount of inputted light, an excessive raise in the electron multiplication factor causes saturation. Therefore, to adjust the electron multiplication factor is effective in order to avoid such saturation of the sensor when the considerable amount of light enters the electron multiplying CCD sensor.

The adjustment of the electron multiplication factor may be performed real time according to the output of the electron multiplying CCD sensor. Alternatively, it may be performed on the basis of information inputted in advance by an operator, or design information of the subject inputted in advance, or information about manufacturing conditions of the manufacturing process of the subject, or information about amount of light actually gained by conducting measurement of the subject by using present invention or by using other inspection/observation device in advance on each of the subjects or at every different position on the subject.

As a method to avoid saturation of the electron multiplying CCD sensor due to the above input of great amount of light, there also are a method to adjust the amount of illuminating light, a method to selectively shade/attenuate background light, etc. Further, by providing the electron multiplying CCD sensor with an anti-blooming characteristic, it is possible to prevent the influence to neighboring pixels when the amount of light exceeding the saturation amount of light enters a certain pixel.

It is possible to achieve a method of adjusting the amount of illuminating light by controlling the output of a light source or providing a beam attenuating means such as an ND filter in the illumination optical system and controlling an attenuating rate, and so on.

Further, a method to selectively shade/attenuate the background light can be achieved, for example, by providing the detection optical system with a spatial filter etc. and selectively shading/attenuating the zero-order diffraction light or higher-order diffraction light from a pattern, and so on.

Further, by providing the electron multiplying CCD sensor with a plurality of output taps, detection signals can be outputted in parallel. By parallel-processing the signals outputted in parallel, a high-speed inspection is made possible.

Further, the device of the present invention can cover from weak light to a large amount of light by using both the electron multiplying CCD and the CCD sensor not multiplying electrons as the photo-detectors of the device for inspecting foreign matters and defects, and by detecting weak light with the electron multiplying CCD sensor and detecting relatively strong light with the CCD sensor which does not multiply electrons. Thus, it is becomes possible to conduct highly sensitive/wide dynamic-range inspection. The construction of the present device may be basically the same as that of the conventional device for inspecting foreign matters and defects, and the optical path of the detection optical system may be branched into two on the way and the electron multiplying CCD sensor and the CCD sensor which does not multiply electrons may be provided in respective optical paths. Alternatively, in addition to the detection optical system of the conventional device for inspecting foreign matters and defects, there may be provided another inspection optical system.

According to the present invention, by using the electron multiplying CCD sensor as a photo-detector of the device for inspecting foreign matters and defects, it is possible, with basically the same construction as that of the conventional device for inspecting foreign matters and defects, to conduct a highly sensitive inspection at the speed faster than the conventional device, or to conduct an inspection at high speed with higher inspection sensitivity than the conventional device, or to conduct a highly sensitive or high-speed inspection with the illumination whose output is lower than the conventional device and without giving damage to the subject.

These and other objects, features and advantages of the invention will be apparent from the following more particular description of preferred embodiments of the invention, as illustrated in the accompanying drawings.

BRIEF DESCRIPTION OF THE DRAWINGS

Embodiments of the present invention will be described in detail based on the following figures, wherein:

FIG. 1 is a schematic diagram showing an embodiment of the present invention;

FIG. 2 is a view showing a direction of the illuminating light by the illumination system of FIG. 1;

FIG. 5A is a perspective view showing an outside shape of an on-chip electron multiplying CCDS sensor 4 of FIG. 1 and FIG. 5B shows a pixel configuration;

FIG. 6A is a schematic diagram of an example wherein a plurality of output taps is provided in the electron-bombarded multiplying CCD sensor and FIG. 6B is a schematic diagram of an example wherein a plurality of output taps is provided in the on-chip electron multiplying CCD sensor;

FIG. 7 is a block diagram to explain how to adjust an electron multiplication factor of the electron multiplying CCD sensor of FIG. 1:

FIG. 8 shows a method of filtering by a spatial filter shown in FIG. 1;

FIG. 15 is a view to explain a detection direction of the detection optical system of FIG. 14;

FIG. 18 is a schematic diagram to explain a construction for reducing coherency in the illumination optical system of FIG. 1;

FIG. 24 is a graph to show examples of calculation of the set correction value of inspection sensitivity shown in FIG. 23.

DESCRIPTION OF THE PREFERRED EMBODIMENTS

Figure 3:
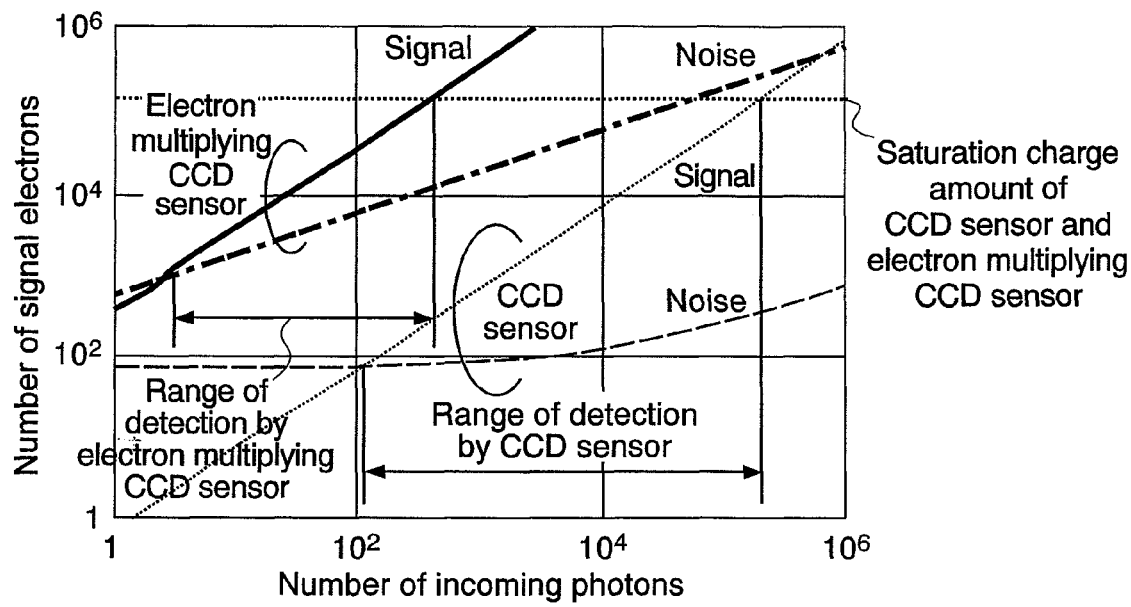
FIG. 3 is a graph showing an example of the ranges of detection by an electron multiplying CCD sensor and an ordinary CCD sensor.

Now, referring to the drawings, embodiments of the present invention will be described. An inspection of foreign matters or defects on a semiconductor wafer will be described, as an example, as follows.

FIG. 1 shows an example of a device detecting foreign matters or defects on a semiconductor wafer. The device of FIG. 1 comprises an illumination controller 1, an illumination system 200, a subject (semiconductor wafer) W, a detection optical system 300, an electron multiplying CCD sensor 4, a signal processor 5, an overall controller 6, a display 7, a memory 8, an input-output unit 9, a computing unit 10, a stage driving unit 11, a stage 12, and a sensor controller 13. The illumination system 200 comprises a light source 201 and an illumination optical system 202. The detection optical system 300 comprises an objective lens 301, a spatial filter 302 removable by a moving means (not shown), and a tube lens 303.

Now, workings of the device will be described. First, the subject W to be inspected is illuminated obliquely by the illumination system 200, scattered light from the subject W mounted on the stage 12 is collected by the objective lens 301 placed above, and the light collected is detected by the electron multiplying CCD sensor 4 via the spatial filter 302 and through the tube lens 303. The signals detected by the electron multiplying CCD sensor 4 are processed by the signal processor 5 and foreign matters or defects are judged. The result of the judgement is displayed on the display 7 by the overall controller 6 or stored in the memory 8. Further, information about the size, location, etc. of the foreign matters or defects is specified by the computing unit 10.

As the light source 201, for example, laser light sources such as an Ar laser, an excimer laser, an F2 laser, a semiconductor laser, a YAG laser, a UV laser, etc. or lamp sources such as an Xe lamp, an Hg lamp, a metal halide lamp, a halogen lamp, etc. are used.

Now, selection of the light source 201 will be described. The intensity of the light scattered from each minute particle is inversely proportional to the fourth power of a wavelength when the particle diameter is smaller than the wavelength. Therefore, in order to detect a minute foreign matter smaller than 100 nm with high sensitivity, it is preferable to use, as the light source 201, a light source with a shorter wavelength. In such a case, preferred light sources are a YAG laser (wavelength: 213 nm, 266 nm, 355 nm), an excier laser (wavelength: 193 nm, 248 nm), an F2 laser (wavelength: 157 nm), an Hg lamp (wavelength: 185 nm, 254 nm, 297 nm, 302 nm, 313 nm, 365 nm, 405 nm, 436 nm), a UV laser, etc.

When the compact and economical light source 201 is desired, a semiconductor laser etc. are preferable. Further, when the economical illumination optical system 202 or inspection optical system 300 is desired, preferred light sources as light sources of visible light are an Ar laser (wavelength: 458 nm, 488 nm, 515 nm), a YAG laser (wavelength: 532 nm), an Hg lamp (wavelength: 546 nm, 577 nm, 579 nm), an Xe lamp, a halogen lamp, etc. Further, when trying to reduce interference by a thin film formed on the subject W, a white light source is preferred as the light source 201. Further, in the detection optical system 300, when conducting spatial filtering by using the spatial filter 302 to be described later as optical processing, a light source emitting a monochromatic parallel light is preferable as the light source 201.

Figure 17:
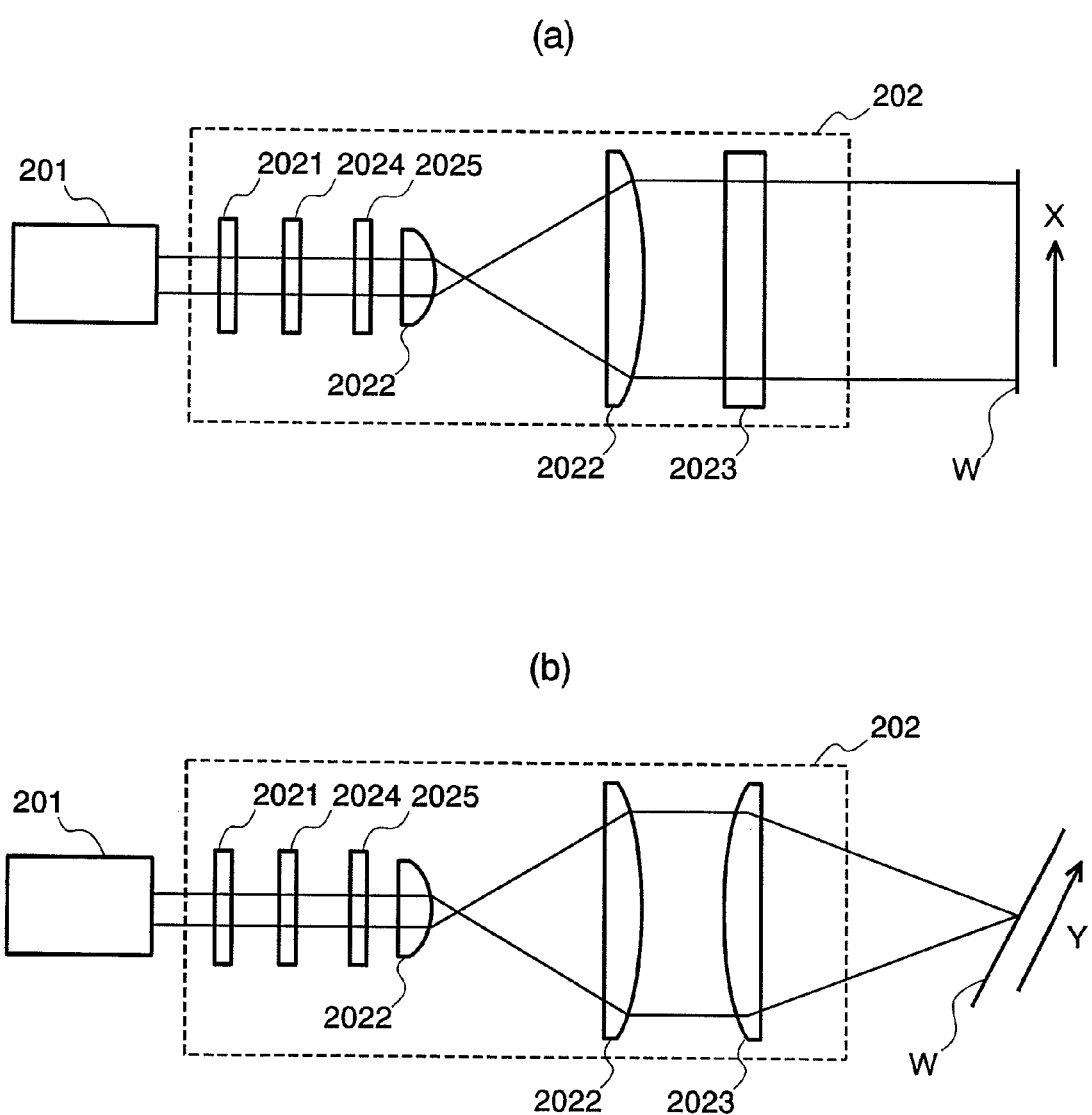
FIG. 17 is a schematic diagram showing a construction of an illumination optical system of FIG. 1.

FIG. 17 shows a configuration of the illumination optical system 202. As shown in FIG. 17A, the illumination optical system 202 provide parallel light beams with respect to the X direction, being collected in the Y direction as shown in FIG. 17B. Namely, the illumination optical system 202 performs linear illumination being longitudinal in the X direction. According to the construction shown in FIGS. 17A and 17B, the illumination optical system 202 comprises a beam attenuating means 2021 such as an ND filter, a beam expander 2022, a cylindrical lens 2023, a polarizing plate 2024, a wavelength plate 2025, etc.

In this construction, an attenuating rate of the beam attenuating means 2021 is variable, and by using this, the amount of light irradiated to the subject W can be controlled. By using the polarizing plate 2024 and the wavelength plate 2025, state of polarization of the light irradiated to the subject W can be controlled. The illumination optical system 202 is adjusted so that the light in the Y direction alone is collected by using the beam expander 2022 and cylindrical lens 2023, and the light is brought to the focal point of the detection optical system 300 on the subject W. The outline of the irradiated range may be linear, circular, or rectangular, so long as it is possible to illuminate the region of the surface of the subject W at the same time where an image is provided on the imaged pixels of the electron multiplying CCD sensor 4.

When using a laser with high coherency as a light source 201, speckles which turn to be noises during inspection are apt to occur. In order to reduce the speckles, a means may be provided in the illumination optical system 202 to reduce coherency of the illuminating light. As a means to reduce coherency, for example, a plurality of optical fibers, quartz plates, glass plates, etc. are used to produce a plurality of luminous fluxes having different optical path lengths to each other and to superpose them. Alternatively, a rotary dispersion plate may be used to reduce coherency. As an example of the illumination optical system 202 providing linear illumination by reducing coherency, FIGS. 18A and 18B show a system as in FIGS. 17A and 17B except that a plurality of quartz plates 2026 having different optical path lengths to each other shown in FIG. 18C is provided between the beam expander 2022 and the cylindrical lens 2003. In the constructions shown in FIGS. 18A and 18B also, the beam attenuating means 2021, polarization plate 2024, and wavelength plate 2025 shown in FIGS. 17A and 17B are provided, though they are not shown in FIGS. 18A and 18b.

With respect to the direction of the illuminating light to the subject W by the illumination system 200, as shown in FIG. 2, an elevation angle $\alpha$ and an azimuth angle $\theta$ of illumination are set. The elevation angle $\alpha$ and azimuth angle $\theta$ of illumination with respect to the subject W may be variable. When the surface of the subject W is covered with a transparent film or a semitransparent film, it is possible to detect foreign matters/defects existing in such a film, for example, by illuminating at an elevation angle $\alpha$ of illumination greater than an elevation angle at which total reflection is caused by the film. Further, it is possible to detect foreign matters/defects on the film surface without detecting foreign matters and defects in the film by illuminating at an elevation angle $\alpha$ of illumination smaller than the elevation angle at which total reflection occurs.

Further, when an uneven pattern is formed on the subject W, in order to inspect foreign matters or defects near the pattern, it is effective to illuminate at a large elevation angle $\alpha$ of illumination so that such an area is illuminated. On the contrary, when the periphery of the pattern should not be inspected, illumination may be provided at a small elevation angle $\alpha$ of illumination so that such an area is not illuminated. Further, when inspecting one side alone of the pattern, the azimuth angle $\theta$ of illumination may be changed or the stage 12 may be rotated in the direction of the angle $\theta$ so that such an area may be illuminated.

Further, as compared to Mie scattering which takes place when the size of a foreign matter is equal to or larger than the illumination wavelength, Rayleigh scattering which takes place when the size of a foreign mater is smaller enough than the illumination wavelength has a greater ratio of back scattering. Therefore, illumination at a wider elevation angle wherein back scattering light is easy to catch in the detection optical system 300 is preferred for detecting very small foreign matters. The elevation angle $\alpha$ of illumination with respect to the subject W can be variable within the range where it does not interfere with the detection optical system 300. For example, when an NA of the detection optical system 300 is 0.6, the elevation angle $\alpha$ of illumination may be sequentially variable within a range, for example, between 20 and 520. Alternatively, the elevation angle $\alpha$ may be selectable from among, for example, 3°, 5°, 1°, 15°, 20°, 30°, 45°, etc.

Further, when the NA of the detection optical system 300 is 0.8, the elevation angle $\alpha$ of illumination may be sequentially variable, for example, within the range between 2° and 3°. Alternatively, it may be selectable from among the angles such as, for example, 3°, 5°, 10°, 15°, 20°, and 30°. The azimuth angle θ of illumination with respect to the subject W is selected according to relative orientation with a pattern. For example, when trying to detect defects such as a short circuit between wiring, illuminating light may enter at an azimuth angle θ of illumination such that the illuminating light is incident in parallel with the wiring. Further, when the pattern has orientation in the horizontal direction (θ=0°) and in the direction of depth perpendicular to the horizontal direction, defects etc. related to patterns in respective directions or defects etc. related to the direction perpendicular to them can be detected by using an azimuth angle θ of illumination in the horizontal direction (θ=0°, 180°) or in the depth direction (θ=±90°). Still further, when trying to detect defects etc. related to the horizontal and depth directions in a well balanced manner, the azimuth angle θ of illumination may be set in the middle direction (for example, in the direction of ±45°, ±135°) between the horizontal direction and the depth direction.

A plurality of both or either of the light source 201 and illumination optical system 202 may be provided. For example, illumination may be provided by a plurality of light sources having different wavelengths from each other. Accordingly, for example, it is possible to make the effects of the interference caused by the thickness of the transparent film even and to stably detect the defects. Further, for example, the light emitted from a single light source may be divided into two or more and the illumination may be provided at elevation angles α of illumination different from each other. Accordingly, it is possible, for example, to detect foreign matters/defects in the transparent film and foreign matters/defects on the surface of the transparent film at the same time. Also, it is possible to make the effect of the interference caused by the thickness of the transparent film even and to detect defects stably. Further, for example, the light emitted from a single light source may be divided into two or more beams of light and the illumination may be provided at an azimuth angles θ of illumination different from each other. Accordingly, it becomes possible to reduce the region hidden in the shadow of the pattern having a certain thickness and to expand the region to be inspected.

The stage 12 has a mechanism which is, for example, capable of moving the subject W into the plane (X-Y plane) perpendicular to the optical axis of the objective lens 301, moving the subject W in the direction (Z) of the optical axis, and rotating the subject W in the X-Y plane.

As driving systems of the stage driving unit 11, there are a system to convert the rotational movement of the rotary motor into linear movement by using a screw mechanism and a system by using a linear motor. The system to convert the rotary movement of the rotary motor into the linear movement by using the screw mechanism has, as compared to the system to use a linear motor, advantages such as being easy to be made compact, being economically made, etc.

On the other hand, compared to the system to convert the rotary movement of the rotary motor into the linear movement by the screw mechanism, the system to use the linear motor has advantages such as being capable of driving at high speed, with high acceleration, with high precision, etc. In the system using the linear motor, if a tunnel actuator as described in U.S. Pat. No. 3,395,155 is used as a linear motor in particular, a fast driving of over 600 mm/s at an acceleration of 40G is possible. The inspection at high speed can be achieved by driving the stage 12 at high speed by such a stage driving unit 11, and compensating for reduction in the amount of light caused by the decrease in storing time during the high-speed scanning by the highly sensitive detection using the electron multiplying CCD sensor 4.

The detection optical system 300 comprises an object lens 301 and a tube lens 303 so that, of the light emitted by the illumination optical system 202, the scattered beams of light from the subject W are focused on the electron multiplying CCD sensor 4. In this regard, the performance of detecting foreign matters is improved if the efficiency of the detection optical system 300 for collecting scattered light is enhanced. Further, in order to change/adjust the optical characteristics of the scattered light from the above subject W, the detection optical system 300 may comprise an optical processing means conducting beam attenuation, shading of the light, phase modulation, etc. with respect to a given position component, a given angle component, a given polarization component, or a given wavelength component.

Now, as an example of the above optical processing means, a method to selectively remove or reduce diffracted light from periodic patterns formed on the subject W by using the spatial filter 302. From the periodic patterns, the diffracted light is emitted at discrete angles satisfying the diffraction condition (FIG. 8A). When the objective lens 301 is placed at a position a focusing distance f of the objective lens 301 away from the surface of the subject W, the light collecting focusing position on the surface (pupil surface 304) 2f away from the surface of the subject W from which the light is emitted depends on the angle at which the light is emitted from the subject W. Namely, optical components emitted from the subject W at the same angle are collected (focused) at the same position on the pupil surface 304 (FIG. 8B).

Figure 9:
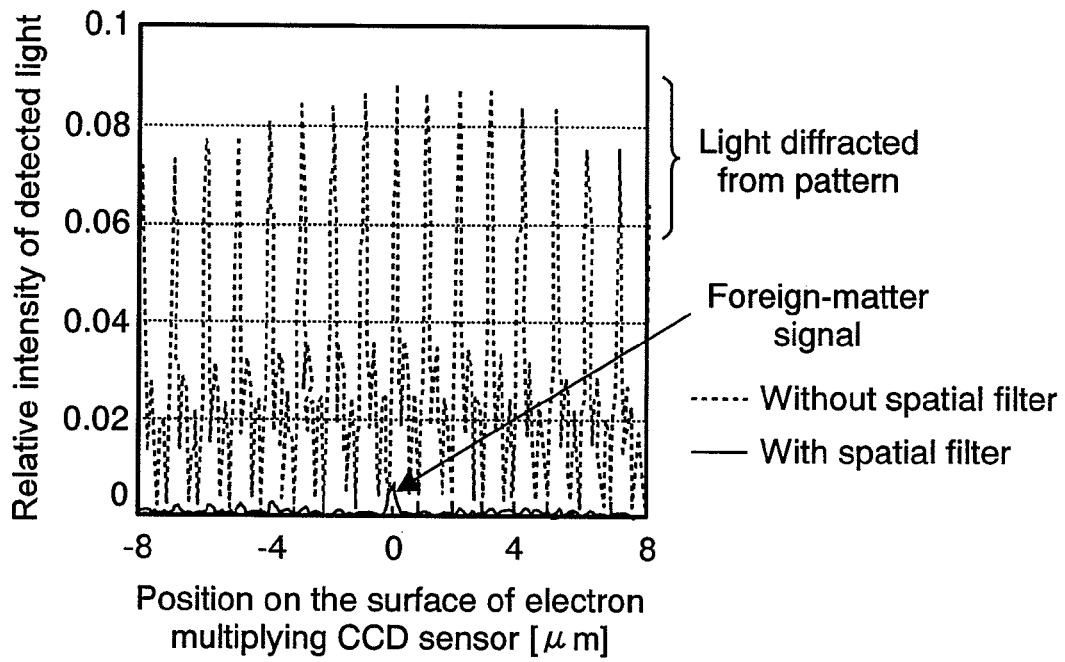
FIG. 9 is a graph to explain an effect of the spatial filter shown in FIG. 1.

The light intensity on the pupil surface 304 is discretely distributed in accordance with the angle at which the diffracted light is emitted. Thus, filtering is performed by using the spatial filter 302 so as to selectively shade/attenuate light diffracted from the patterns discretely distributed. FIG. 8C shows intensity distribution on the pupil surface when the patterns on the subject W are banded patterns having periodic characteristic in the X direction. Also, FIG. 8D shows an example of the spatial filtering. Further, FIG. 9 shows an example of the effect of the spatial filtering. In order to conduct an inspection suitable for the construction of the pattern formed on the subject W, the spatial filter 302 is desirable if the position at which light shading, beam attenuation, or phase modulation is conducted on the filter surface is variable. For example, a shading plate capable of mechanically control the light shading position, a liquid crystal optical element capable of electrically control the position, etc. are used.

When the detection optical system 300 is a Fourier transform optical system, the diffracted light from the periodic pattern forms luminescent spots or bright lines at the same pitch on the Fourier transform surface. Therefore, as the spatial filter 302, such a filter means may be used that shades light, attenuate beams, or conducts phase modulation of the predetermined width at variable same pitch on the Fourier transform surface. In this regard, when light-collecting illumination is provided by using said illumination optical system 202, with respect to the diffracted light from the repetitive patterns formed on the subject W, in conducting spatial filtering by the spatial filter 302 to be described later in the detection optical system 300, by using the illumination optical system 202, and by irradiating illuminating light which is at least in parallel with the repetition direction, the spread of the angle of the diffracted light from the repetitive patterns in the repetition direction is suppressed, enabling the effective filtering.

The electron multiplying CCD sensor 4 is the one which receives the scattered light collected by the detection optical system 300 and conducts photoelectric conversion, and is capable of electron multiplication processing in which electrons produced by the photoelectric conversion are multiplied. To be used as such an electron multiplying CCD sensor 4 are, for example, an electron-bombarded multiplying CCD sensor described in Japanese Patent Laid-open No. 11-204072 which multiplies electrons by causing an electron-bombardment multiplication, an on-chip electron multiplying CCD sensor described in U.S. Pat. No. 5,337,340 which multiplies electrons by causing impact ionization during an electron transfer, etc.

FIG. 3 shows an example of detection ranges of the electron multiplying CCD sensor and an ordinary CCD sensor. The electron multiplying CCD sensor is capable of relatively enlarging the signals generated by the inputted light with respect to electric (cal) noises by reading the electrons produced by the photoelectric conversion after multiplying them. Therefore, compared with the ordinary CCD sensor which does not multiply electrons, it is capable of detecting weaker light. Further, like the ordinary CCD sensor, it is capable of imaging more than 1,000 pixels at the same time and reading them at high speed. Still further, its electron multiplication factor is variable.

Figure 4:
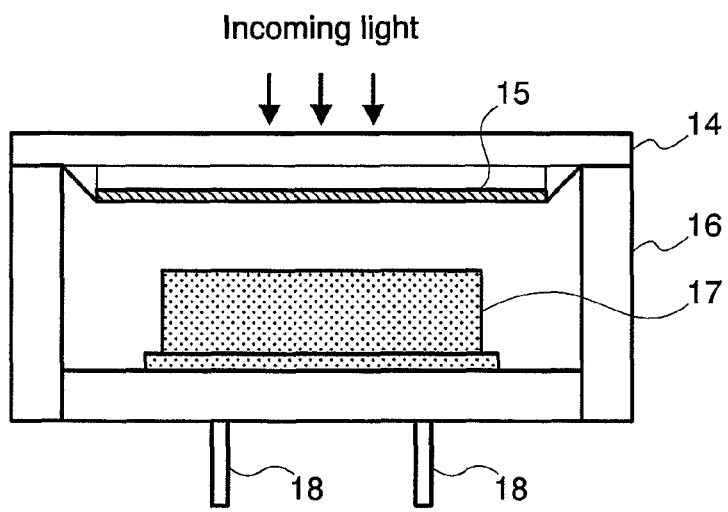
FIG. 4 is a cross section showing a schematic construction of an electronic-bombarded multiplying CCD sensor.

As an example of the electron multiplying CCD sensor 4, FIG. 4 shows a construction of the electron-bombarded multiplying CCD sensor. The electron-bombarded multiplying CCD sensor comprises a window member 14, an photoelectric-conversion surface 15, a vacuum package 16, a built-in CCD sensor 17, output pins 18, and a means (not shown) to apply voltage between the photoelectric conversion surface 15 and the built-in CCD sensor.

The light having passed through the window member 14 and entered the photoelectric conversion surface 15 is photoelectric-converted and photoelectrons are generated from the photoelectric conversion surface 15. The generated photoelectrons are accelerated by the voltage (for example, from 100 V to 8 kV) applied between the photoelectric conversion surface 15 and the built-in CCD sensor 17, and collided against the built-in CCD sensor 17 with high energy. The electron-bombardment multiplication is caused by this collision, and a large number of electrons (for example, 25 to 2,000 electrons from one photoelectron) are generated in the built-in CCD sensor 17. The electron multiplication factor depends on the voltage applied between the photoelectric conversion surface 15 and the built-in CCD sensor 17. The multiplied electrons are read after having been transferred vertically and horizontally in the built-in CCD sensor 17, and signals are outputted from the output pins 18.

A back-side irradiating CCD element is used for the built-in CCD sensor 17. This is because if a front-side irradiating CCD element is used, the constructions such as gate electrodes formed on the front surface are destroyed by the electron bombardment with high energy. Further, the built-in CCD sensor 17 must be vacuum resistant. Still further, a construction or material which hardly produces outgas may be used to prevent the degradation due to vacuum inside the vacuum package 16.

As another example of the electron multiplying CCD sensor 4, FIGS. 5A and 5B show a construction of the on-chip electron multiplying CCD sensor. The outside shape of the on-chip electron multiplying CCD sensor (FIG. 5A) is similar to that of a conventional CCD sensor. However, as shown in FIG. 5B, it is different from the conventional CCD sensor in that an electron multiplying transfer unit 21 conducting electron multiplying transfer is provided between a vertical transfer unit 19/a horizontal transfer unit 20 and a signal outputting unit 22 performing charge voltage conversion.

In the electron multiplying transfer unit 21, by giving a greater transfer pulse than during an ordinary vertical/horizontal transfer, impact ionization is caused by electrons fell in the deep potential well and the number of electrons increases. For example, if the electron multiplication factor per one column of the electron multiplying transfer unit 21 is 101% and 500 columns of electron multiplying transfer is conducted, the number of electrons increases 145 times after the transfer. The electron multiplication factor depends on the size of the transfer pulse given in the electron multiplying transfer unit 21.

Figure 20:
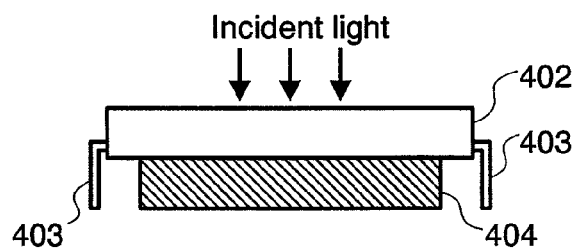
FIG. 20 is a schematic diagram to explain a construction of a cooling means of the on-chip multiplying CCD sensor of FIG. 5.

The on-chip electron multiplying CCD sensor can be designed such that the saturation charge amount of the electron multiplying transfer unit is greater than the saturation charge amount of imaged pixels. By using so designed on-chip electron multiplying CCD sensor as an electron multiplying CCD sensor 4, while maintaining the pixel size of the imaged pixels, it is possible to reduce the chance of saturation taking place in the electronic multiplying transfer unit 21 due to signal electrons during electron multiplication. The heat of the electron multiplying transfer unit 21 of the on-chip electron multiplying CCD sensor may cause change in the electron multiplication factor and or a malfunction in the sensor itself. In order to prevent this, for example, as shown in FIG. 20, a cooling means may be provided, such as having a Peltier element 404 contact the back surface of the substrate 402 of the on-chip multiplying CCD sensor.

In this regard, as the electron multiplying CCD sensor 4, when trying to obtain a two-dimensional image, an electron multiplying CCD sensor of two-dimensional area type is used. When trying to obtain a one-dimensional image or wishing to obtain a two-dimensional image by scanning a one-dimensional field of view, an electron multiplying CCD sensor of one-dimensional line type or, in order to raise (enhance) the sensitivity, an electron multiplying CCD sensor which performs TDI (Time Delay Integration) operation is used.

FIG. 1 shows a case where the electron multiplying CCD sensor 4 performs A/D conversion inside and digital output. When using a CCD sensor of analog output type, it may be constructed such that an A/D conversion means is provided before the signal processor 5 to convert analog signals into digital signals, which are then outputted to the signal processor 5.

As the electron multiplying CCD sensor 4, the one having sensitivity in the wavelength region of the illuminating light to be used. For example, in the case of the electron-bombarded multiplying CCD sensor as shown in FIG. 4, spectral sensitivity characteristics differ according to materials of the photoelectric conversion surface 15 and the window member 14. As the window member 14, the one having high transmissivity at the illumination wavelength may be used. For example, when the illumination wavelength is between 190 nm and 400 nm, a composite quartz or a fluorite, for example, which has high transmissivity at the above wavelength region, is effective. Further, as the photoelectric conversion surface 15, the one made of a material whose quantum efficiency is high at the illumination wavelength is used. For example, when the illumination wavelength is between 190 nm and 400 nm, as a material for the photoelectric conversion surface 15, multi-alkaline, bi-alkaline, Sb—Cs, Cs—Te, etc. are preferred. Further, in the case of the on-chip electron multiplying CCD sensor, whether it is a front-side illumination type or a back-side illumination type greatly influences spectral sensitivity characteristics.

Figure 21:
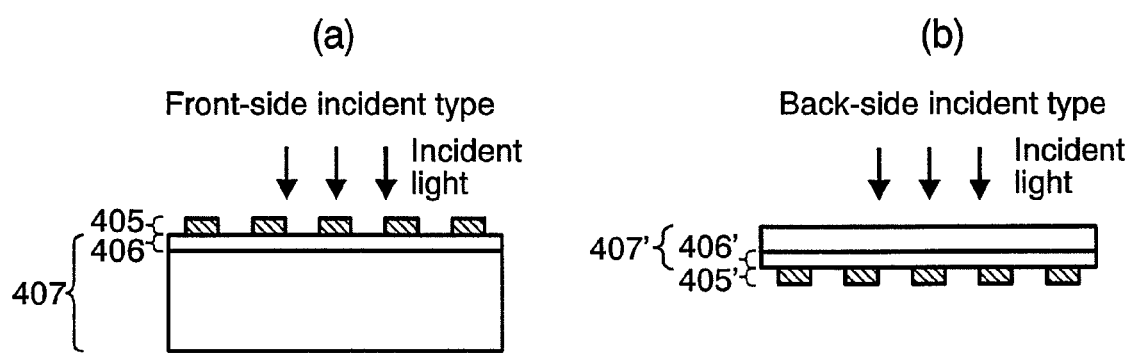
FIG. 21A is a concept diagram showing a front-side illumination type sensor as the on-chip multiplying CCD sensor of FIG. 5
FIG. 21B is a concept diagram showing a back-side illumination type sensor as the on-chip multiplying CCD sensor of FIG. 5.

FIGS. 21A and 21B show cross sections of the front-side irradiation type sensor and the back-side irradiation type sensor, respectively. By the voltage applied to an Si substrate 407 or an Si substrate 407' by a surface electrode 405 or a surface electrode 405', charges are accumulated in a depletion layer formed in a depletion-layer forming region 406 or 406'. The front-side irradiation type sensor has quantum efficiency of more than 50% in a visible light region. However, in a region of a UV light or a DUV light, incident light is absorbed by the surface electrode 405 and does not reach Si substrate 407. Therefore, its quantum efficiency is, for example, less than 10% and the sensor has almost no sensitivity. Even with the front-side irradiating type sensor, there is a method to detect a UV light or a DUV light by applying organic thin film coating on a cover glass so that when the UV light or DUV light enters the visible light is emitted accordingly.

In the case of the back-side irradiation type sensor, it is necessary to shave the Si substrate 407' when manufacturing so that the light entering from the back side reaches the depletion layer forming region 406', and it has a defect that the defective pixels are apt to be produced compared with the front-side irradiation type sensor. However, it is possible to achieve high quantum efficiency of more than 90% even in the visible light region and, even in the UV or DUV wavelength region, it can achieve high quantum efficiency of more than 60%. In view of the above, it is preferable to use the front-side irradiation type sensor or back-side irradiation type sensor when providing illumination with visible light. On the other hand, it is preferable to use back-side irradiation type sensor when illumination is provided with the UV light or DUV light, or using several illumination wavelengths including the UV light, DUV light, etc.

Further, as the electron multiplying CCD sensor 4, the one with a large number of pixels (for example, more than 1,000 pixels) is used. The time required for the inspection can be shortened by imaging a large number of pixels at the same time and by outputting signals at high speed of, for example, 1 GPPS (10 to the 9th power pixels per second).

Generally, when reading signals from a CCD sensor, the more the signal read-out frequency is raised, the greater the electric noise called read-out noise produced during reading signals becomes. As shown in FIGS. 6A and 6B, by providing the electronic multiplying CCD sensor 4 with a plurality of signal output units (22'-1 to 22'-4 or 22-1 to 22-4 in the example of FIG. 6), and by conducting simultaneous parallel output of the signals, net signal output speed can be increased without raising the signal read-out frequency per one signal output unit, namely, without increasing the read-out noise. For example, if the data rate per one signal output unit is 20 MHz, when the number of signal output units is 1, 10, or 50, the signal output rate of 20 MPPS, 200 MPPS, or 1 GPPS, respectively, can be achieved. By parallel processing signals outputted in parallel from the plurality of signal output units in the signal processor 5, a high-speed inspection is made possible.

When using on-chip electron multiplying CCD sensor as the electron multiplying CCD sensor 4, and when providing a plurality of signal output units, as shown in FIG. 6B, each of the electron multiplying transfer units 21-1 to 21-4 must be provided to each of the signal output units 22-1 to 22-4. In such a case, each electron multiplying transfer unit may have different conditions such as structure of the element, temperature, applied voltage, etc., which may cause differences among the electron multiplication factor of the electron multiplying transfer units 21-1 to 21-4. Therefore, it is necessary to compensate for the output difference among the signal output units 21-1 to 22-4 caused by it. Also, when using an electron-bombarded multiplying CCD sensor as the electron multiplying CCD sensor 4, if the charge voltage conversion efficiency etc. of each of the signal output unit 22'-1 to 22'-4 differs, it is necessary to compensate for the signal amount among signal output units 22'-1 to 22'-4.

Figure 25:
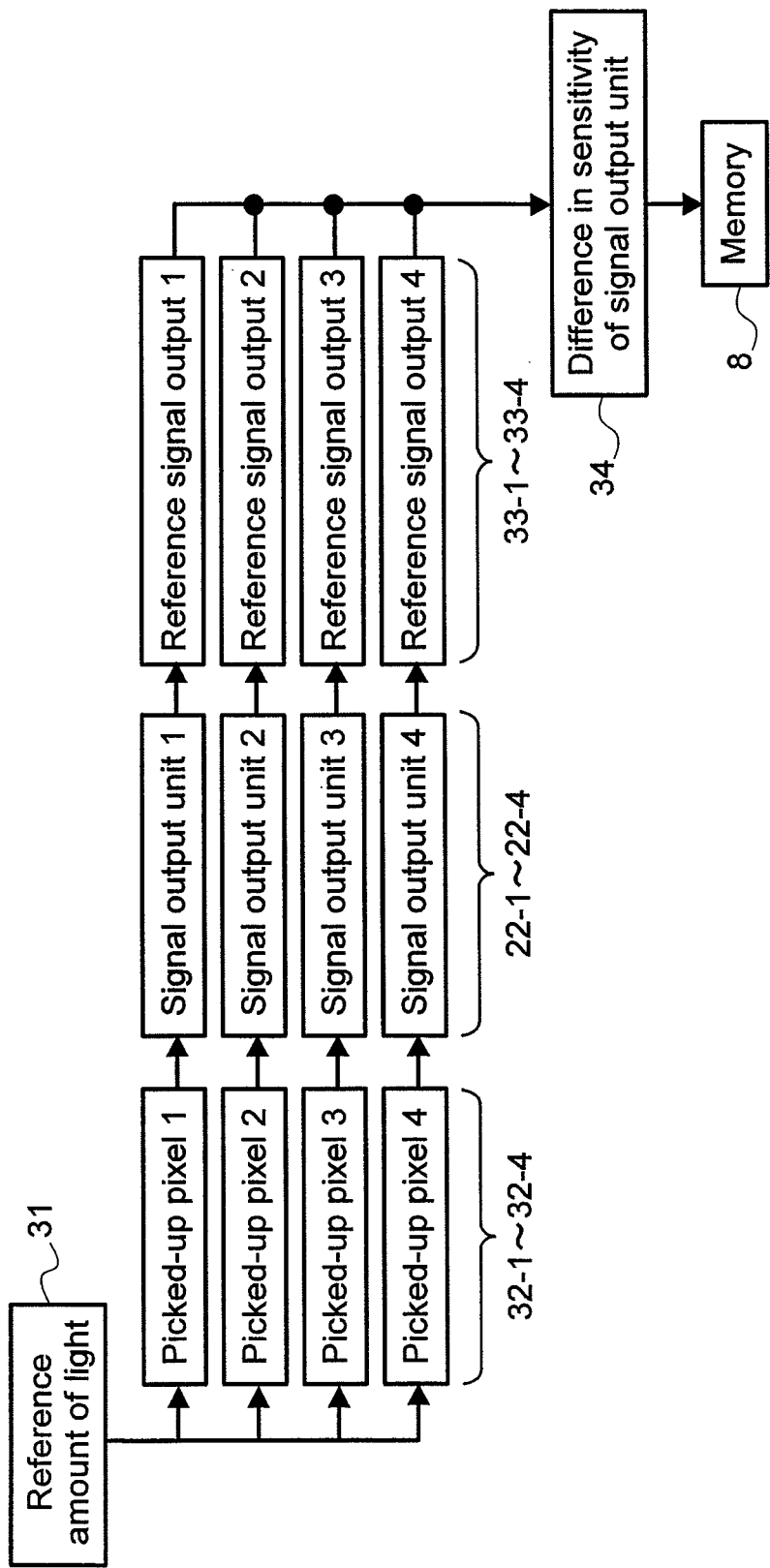
FIG. 25 is a block diagram showing a method to measure a difference in sensitivity of the signal output units shown in FIG. 19.

As shown in FIG. 25, such compensation can be made by storing reference signal output 33-1 to 33-4 used when the reference amount of light 31 is inputted to imaged pixels 32-1 to 32-4 corresponding to respective signal output units 22-1 to 22-4 in advance before the inspection or their ratios as a difference in sensitivity of signal output units 34 in the memory 8 etc., and by using this information during the inspection with a signal amount compensation unit 509 to be described later.

By raising the electron multiplication factor of the electron multiplying CCD sensor 4 or by increasing amount of illuminating light of the illumination system 200, the amount of signal light produced from the subject W is increased and the inspection sensitivity of the foreign matters/defects can be raised. Compared to an ordinary CCD sensor which does not multiply electrons, since the electron multiplying CCD sensor 4 does multiply electrons, a large number of signal electrons are generated inside and it is apt to saturate (FIG. 3). In order to avoid the saturation of the electron multiplying CCD sensor 4 and conduct the highly sensitive inspection, it is effective to conduct the inspection while adjusting the inspection sensitivity such as setting the inspection sensitivity high to raise the sensitivity when inspecting a region whose background light is weak and setting the inspection sensitivity low to prevent the saturation when inspecting a region whose background light is strong.

By adjusting the inspection sensitivity by changing the electron multiplication factor of the electron multiplying CCD sensor 4, it is possible to set a different sensitivity even in a region illuminated at the same time. The adjustment of the electron multiplication factor of the electron multiplying CCD sensor 4 can be made by controlling the voltage to be applied between the photoelectric conversion surface 15 and the built-in CCD sensor 17 when, for example, an electron-bombarded multiplying CCD sensor is used as the electron multiplying CCD sensor 4. Further, when using an on-chip electron multiplying CCD sensor as the electron multiplying CCD sensor 4, it can be achieved by controlling the size of the transfer pulse to be given in the electron multiplying transfer unit 21.

By adjusting the inspection sensitivity through changing the amount of illuminating light from the illumination system 200, even if there exists an region on the subject W where damage might be given by the illuminating light, the inspection can be conducted while damage to the subject is suppressed by lowering the amount of the illumination light. The adjustment of the amount of illuminating light from the illumination system 200 can be made by controlling the output of the light source 201 or by a beam attenuating means 2021 provided in the illumination optical system 202.

FIG. 7A shows an adjusting method of the inspection sensitivity. The adjustment of the inspection sensitivity is conducted on the basis of sensitivity reference information 705 such as, for example, an inspection condition (inspection recipe 701) inputted by the operator, design information of subject W (subject design information 702), information about manufacturing conditions of the manufacturing process of the subject W (subject process condition 703), information obtained by the measurement of the subject W (subject measurement result 704) using an optical- or electron beam-inspection/observation device. The above information is inputted through the input-output unit 9 or, the one held in the memory 8 is used. Based on the above sensitivity reference information 705, an inspection sensitivity set value 706 is calculated and set in the overall control unit 6.

The inspection sensitivity set value 706 is comprised of an electron multiplication factor set value 706A and an amount of illuminating light set value 706B. As the inspection sensitivity set value 706, a different value may be set for each subject W, or each region (for example, for each region in a chip, each chip, each exposed shot, each line) on the subject W.

As a method to calculate the inspection sensitivity set value 706 based on the sensitivity reference information 705, for example, when the subject design information 702 is given, pattern density in every given region on the subject W is evaluated. Then, such calculation is made that the inspection sensitivity set value 706 is relatively low in a region whose pattern density is high and the inspection sensitivity set value 706 is relatively high in a region whose pattern density is low to set the inspection sensitivity value 706.

Further, for example, when the result of the scattered light detection from a plurality of chips on the subject W is given as a measurement result 704 of the subject, the setting may be made by calculating average amount of scattered light of each region in the chip and calculating the inspection sensitivity set value 706 which is inversely proportional to the obtained average amount of scattered light.

Figure 22:
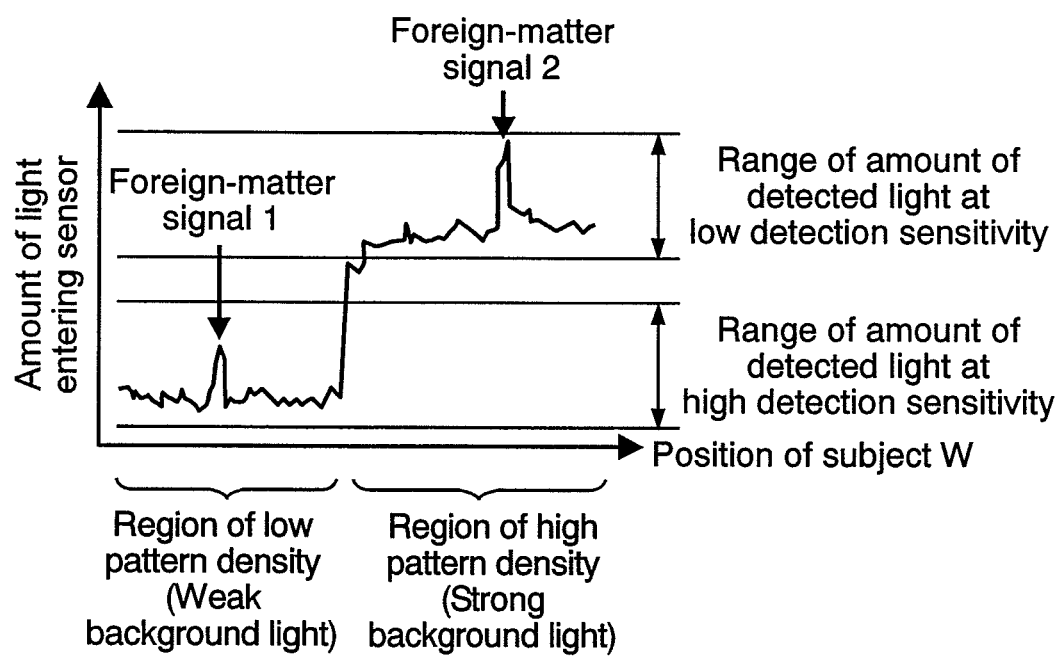
FIG. 22 is a graph to show an example of adjusting inspection sensitivity by controlling the electron multiplication factor of the electron multiplying CCD sensor or amount of illuminating light of the illumination system shown in FIG. 1.

By calculating the inspection sensitivity set value 706 and setting up, saturation in a region whose background scattered light is strong such as a high pattern density region can be prevented, and a region whose background scattered light is weak can be inspected with high sensitivity (FIG. 22).

Figure 23:
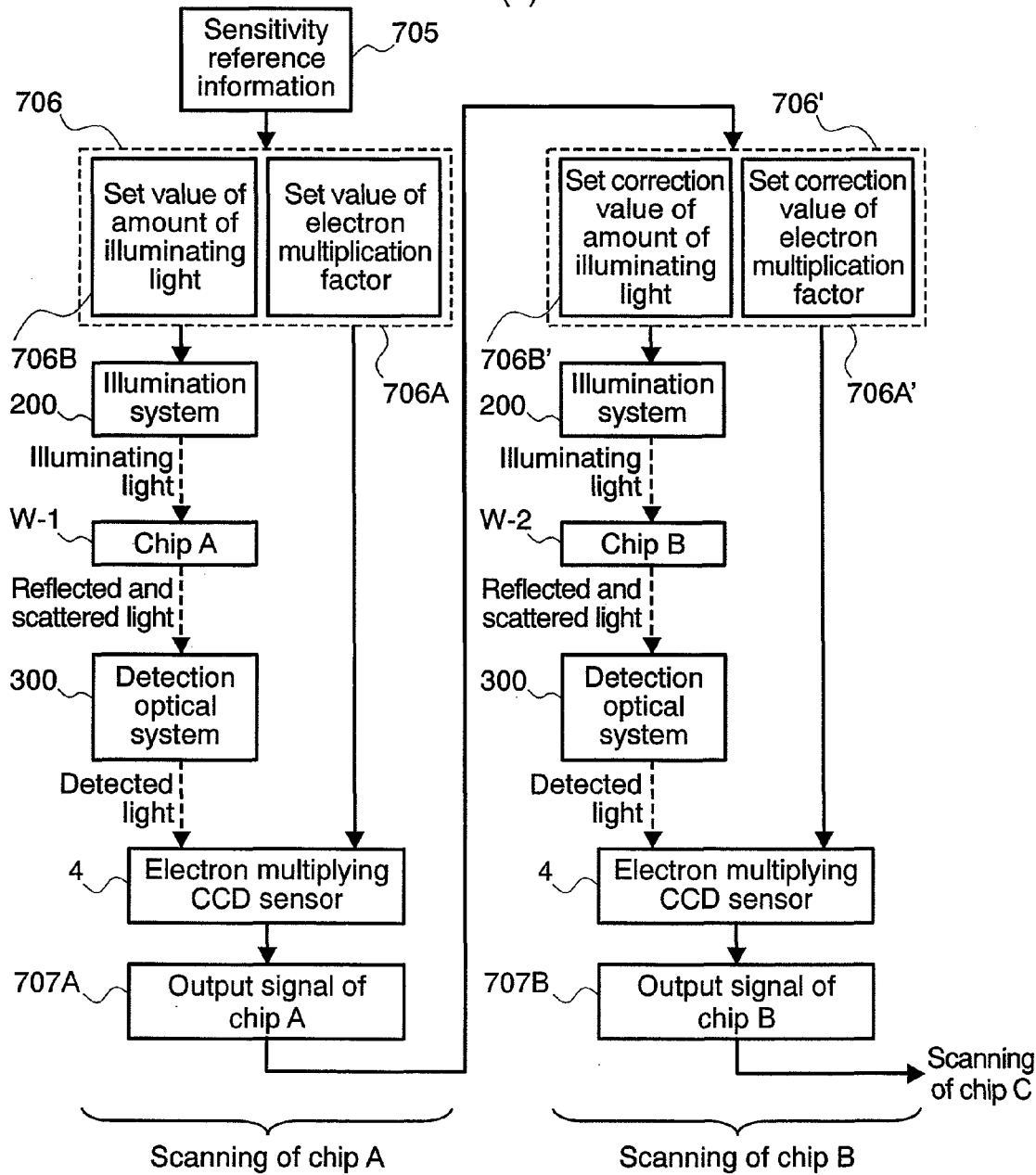
FIG. 23 is a block diagram showing how to correct inspection sensitivity based on the amount of output signals of the electron multiplying CCD sensor of FIG. 1.

In addition to the method of adjusting inspection sensitivity based on the sensitivity reference information 705 obtained in advance as shown in FIG. 7, as an example shown in FIG. 23, the inspection sensitivity 706 may be adjusted by using the output of the electron multiplying CCD sensor 4. Let us consider the case where a chip A (W-1), a chip B (W-2), and a chip C (W-3) on the subject W are scanned and inspected in that order by using the stage 12.

First, the inspection sensitivity set value 706 is set on the basis of the sensitivity reference information 705 by the method shown in FIG. 7. Then, by using the illumination system 200, the chip A (W-1) is illuminated with the amount of illuminating light set on the basis of the amount of illuminating light set value 706B. The reflected scattered light from the chip A is guided to the electron multiplying CCD sensor 4 by using the detection optical system 300. The electron multiplication factor of the electron multiplying CCD sensor 4 is set at the electron multiplication factor set value 706A. Based on the output signal (output signal 707A of the chip A) from the electron multiplying CCD sensor 4, a set correction value 706' of inspection sensitivity is calculated and set in the signal processor 5 or overall control unit 6.

The set correction value 706' of inspection sensitivity is set by giving correction to the set value 706 of inspection sensitivity so that saturation due to excessively high inspection sensitivity or shortage of signal output amount due to excessively low inspection sensitivity may not take place during and after the scanning of the chip B to be carried out after the scanning of the chip A. FIG. 24 shows an example of the calculation of the set correction value 706' of inspection sensitivity. The image formed by the output signal 707A of the chip A is divided into given regions. For example, when a mean value 708 of the output signal in the region is the saturation signal amount or close to the saturation signal amount, the set correction value 706' of inspection sensitivity in the region may be set by multiplying the set value 706 of inspection sensitivity of the region by a coefficient smaller than 1 (one). Further, for example, when the mean value of the output signal in the region is a minimum value of the output signal amount of the electron multiplying CCD sensor 4 or close to it, the set correction value 706' of inspection sensitivity in the region may be set by multiplying the set value 706 of inspection sensitivity in the region by a coefficient greater than 1 (one).

By giving an anti-blooming characteristic to the electron multiplying CCD sensor 4, even when it is saturated, until a predetermined amount of light (, which is anti-blooming charge amount here; for example, charge amount 100 times as much as the saturation charge amount) is exceeded, the charges are prevented from flowing into the pixels in the neighborhood. In order to give the anti-blooming characteristic to the CCD sensor, in general, an anti-blooming gate is provided around the periphery of the imaged pixels of the CCD sensor. However, by providing the anti-blooming gate, a valid pixel area may be reduced and the sensor's sensitivity may be lowered. Though it is possible to increase the ratio of the anti-blooming charge amount against the saturation charge amount by expanding the anti-blooming gate, the sensor's sensitivity is lowered that much. However, since the electron multiplying CCD sensor 4 can increase the sensitivity by raising the electron multiplication factor, the demerit of the decrease in sensitivity caused by providing the anti-blooming gate can be compensated to some extent.

Figure 10:
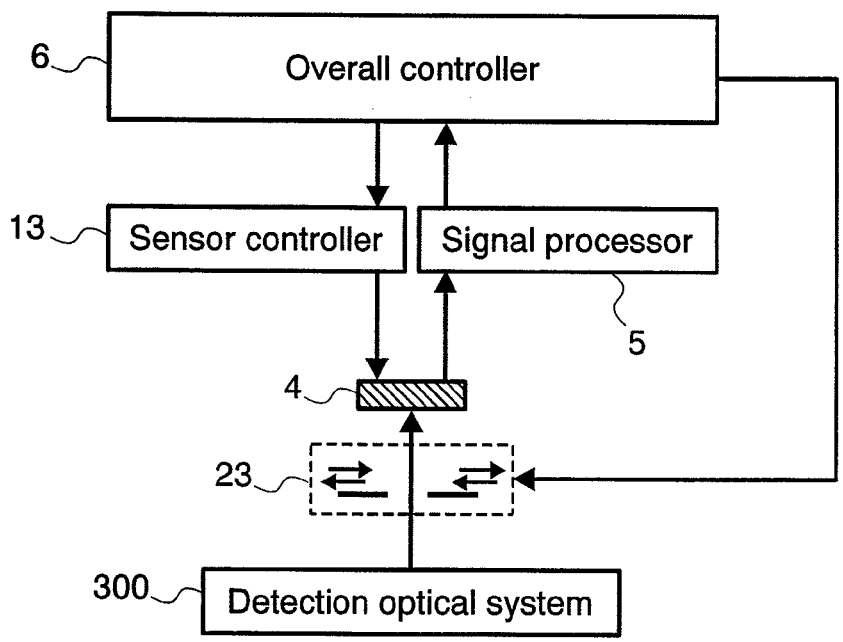
FIG. 10 is a schematic diagram to describe a shutter means to be used when the electronic-bombarded multiplying CCD sensor is used as the electronic multiplying CCD sensor of FIG. 1.

When using an electron-bombarded multiplying CCD sensor as the electron multiplying CCD sensor 4, the sensitivity of the electron-bombarded multiplying CCD sensor may be degraded by the excessive light. Therefore, it is necessary to prevent the excessive light from entering the sensor. This is performed by monitoring the amount of light entering the electron multiplying CCD sensor 4 and promptly reducing the amount of light entering the electron multiplying CCD sensor 4 when a particular threshold value is exceeded. In this regard, for the amount of incident light, information about the absolute amount of incident light before the electron multiplication is used. The information about the amount of incident light is calculated in the signal processor 5, the overall controller 6, etc. on the basis of the sensor signal output and the set value 706A of the electron multiplication factor during the signal output or the correction value 706B of the electron multiplication factor. The amount of light entering the sensor is controlled by controlling the amount of illuminating light by using the same means as in the previously described adjustment of the amount of illuminating light. Alternatively, as shown in FIG. 10, it is carried out by providing a shutter means 23 such as a mechanical shutter on an optical path between the light source 201 and the electron multiplying CCD sensor 4 and by controlling the degree of opened or closed state of the shutter.

Figure 11:
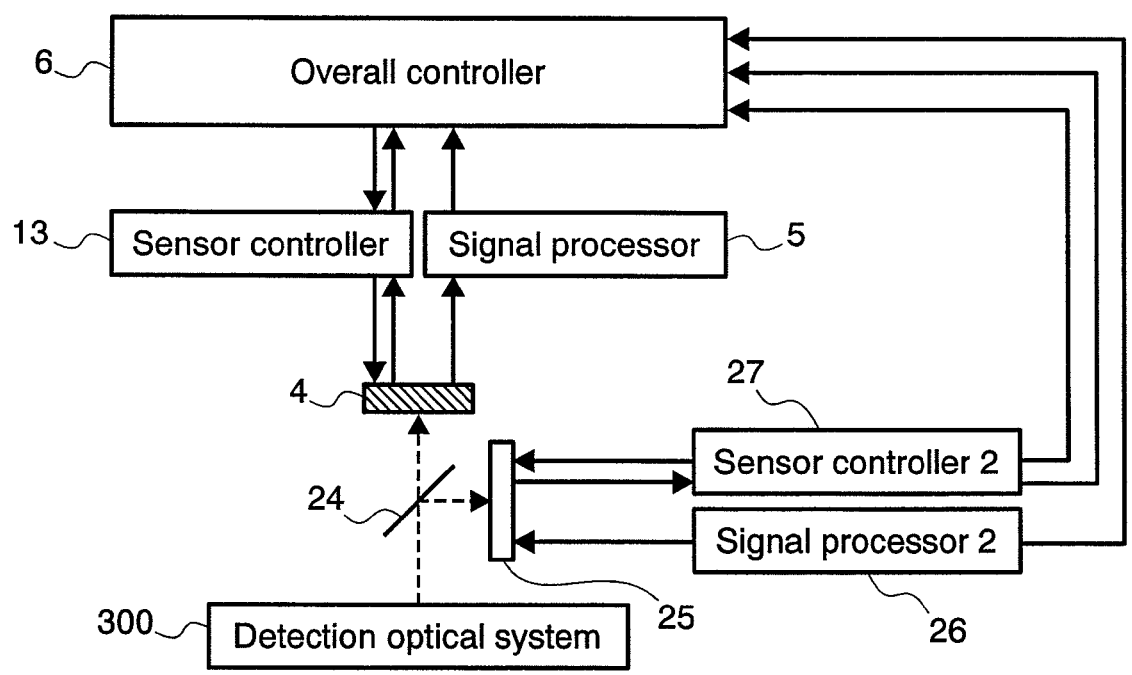
FIG. 11 is a schematic diagram showing a construction wherein both the electron multiplying CCD sensor and CCD sensor which does not multiply electrons are used in the embodiment of FIG. 1.
Figure 19:
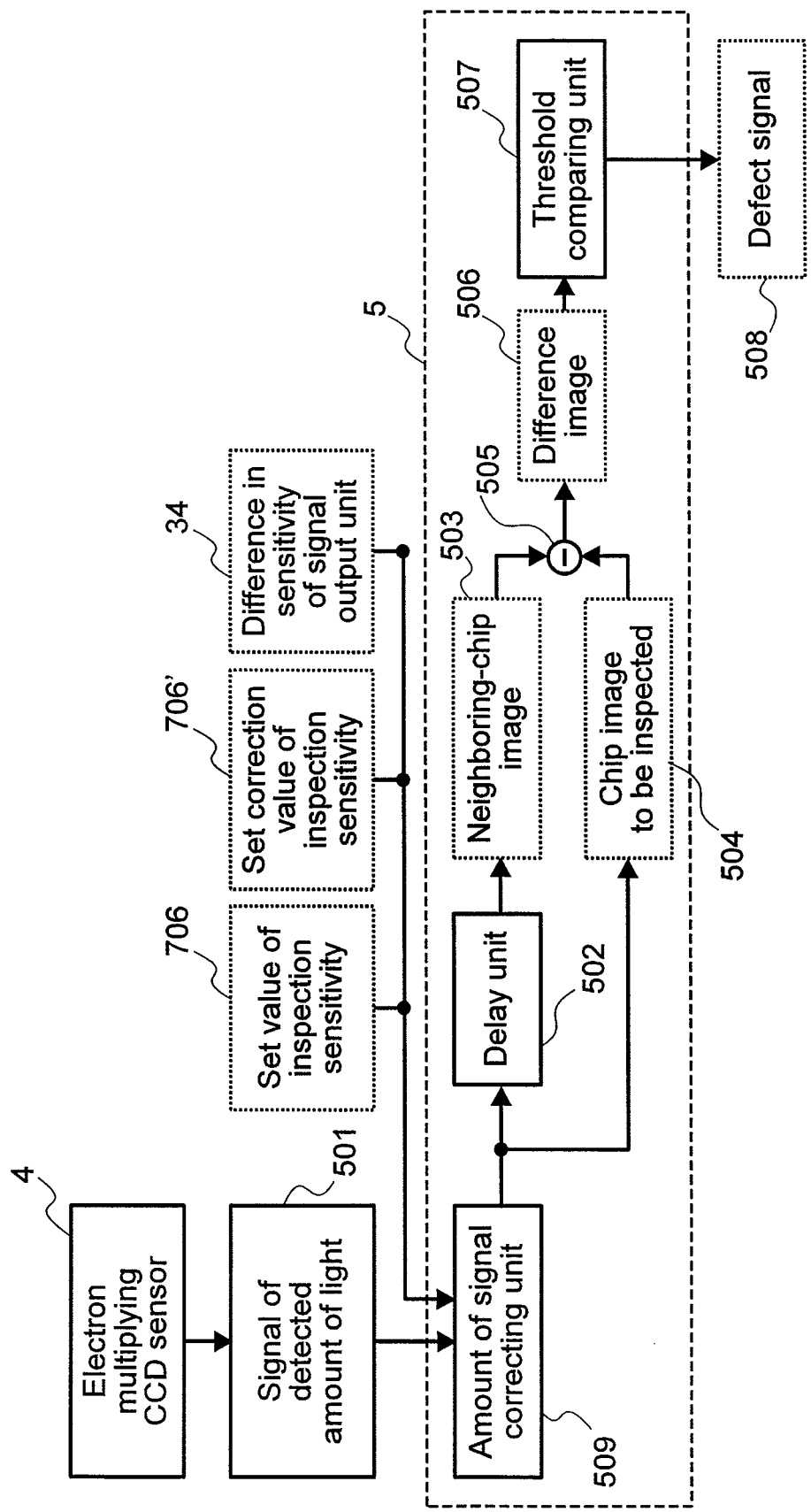
FIG. 19 is a block diagram to explain an example of judging foreign matters/defects by a signal processor of FIG. 1.

Further, by using a CCD sensor which does not multiply electrons in addition to the electron multiplying CCD sensor 4, it is possible to conduct the highly sensitive/wide dynamic range inspection by detecting small amount of light and a great amount of light at the same time. For example, as shown in FIG. 11, it is possible to provide an optical path branching means 24 in the optical path of the detection optical system 300 in basically the same construction as that of FIG. 1, to branch the optical path into two, and to provide the electron multiplying CCD sensor 4 and the CCD sensor 25 which does not multiply electrons on the two optical paths. The intensity ratio of the optical paths after the branching may be 1:1 or may not be 1:1. For example, when the optical path is branched into two with the intensity ratio of 1:1, and when using both the electron multiplying CCD sensor 4 whose minimum detection amount of light is 5 photons and maximum detection amount of light is 1,000 photons (dynamic range 200), and the CCD sensor 25 not multiplying electrons whose minimum detection amount of light is 100 photons and maximum detection amount of light is 100,000 photons (dynamic range 1000), the detection amount of light is 10 photons at a minimum and 200,000 photons at a maximum (dynamic range 20,000), thereby achieving both the high sensitivity and the wide dynamic range The signal processor 5 judges the defects or foreign matters by a method such as comparing the detection results of the same regions of the neighboring chips. For example, as shown in FIG. 19, difference calculation 505 is performed with respect to a chip image 504 to be inspected formed by the signal of detected amount of light 501 gained by scanning the chip to be inspected and a neighboring-chip image 503 gained by delaying, with a delay unit 502, the signal of detected amount of light 501 gained by scanning the neighboring chip right before the chip to be inspected. Further, by comparing the calculated difference image 506 with the binarized threshold by the threshold value comparing unit 507 to binarize it, a signal whose value is greater than the binarized threshold value is judged as a foreign matter or a defective signal 508. The signal processor 5 can also measure the size of a foreign matter from the size of the binarized signal.

A signal correcting unit 509 corrects the signal of amount of light by using a set value 706 of inspection sensitivity or a set correction value 706' of inspection sensitivity. This is because, when the inspection sensitivity is adjusted, a different set value 706 of inspection sensitivity or a different set correction value 706' of inspection sensitivity may be set depending on the inspection position, and it is necessary to correct the difference between signals 501 of detected amount of light caused by the different inspection positions. Also, it is possible to correct the difference between signals of detected amount of light depending on the signal output unit when a plurality of signal output units are provided in the electron multiplying CCD sensor for the signal output unit sensitivity difference, in the signal correcting unit 509 by using the difference in sensitivity of the signal output unit 34.

Figure 12:
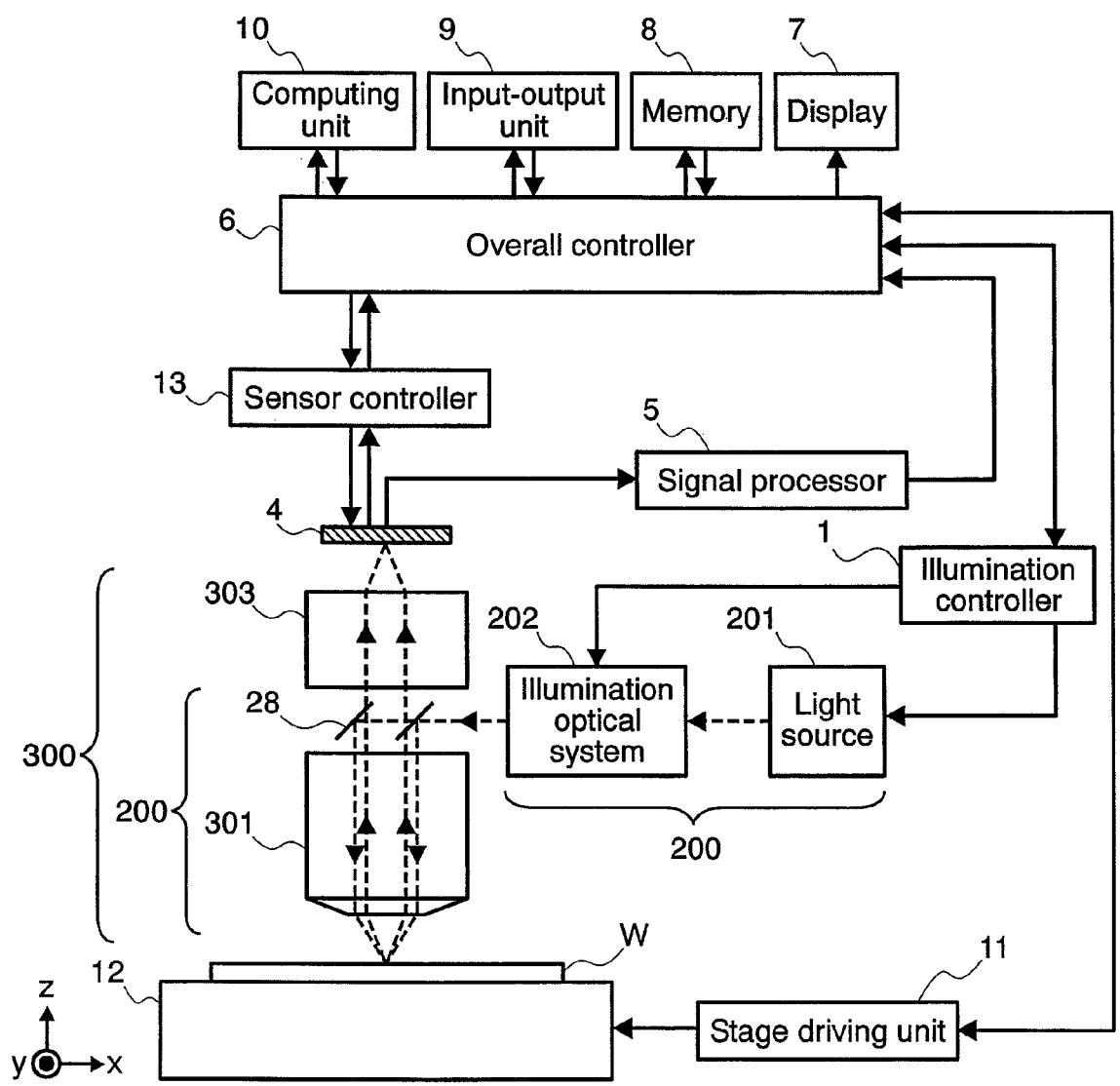
FIG. 12 is a schematic diagram to explain a first modification of the embodiment of FIG. 1.
Figure 13:
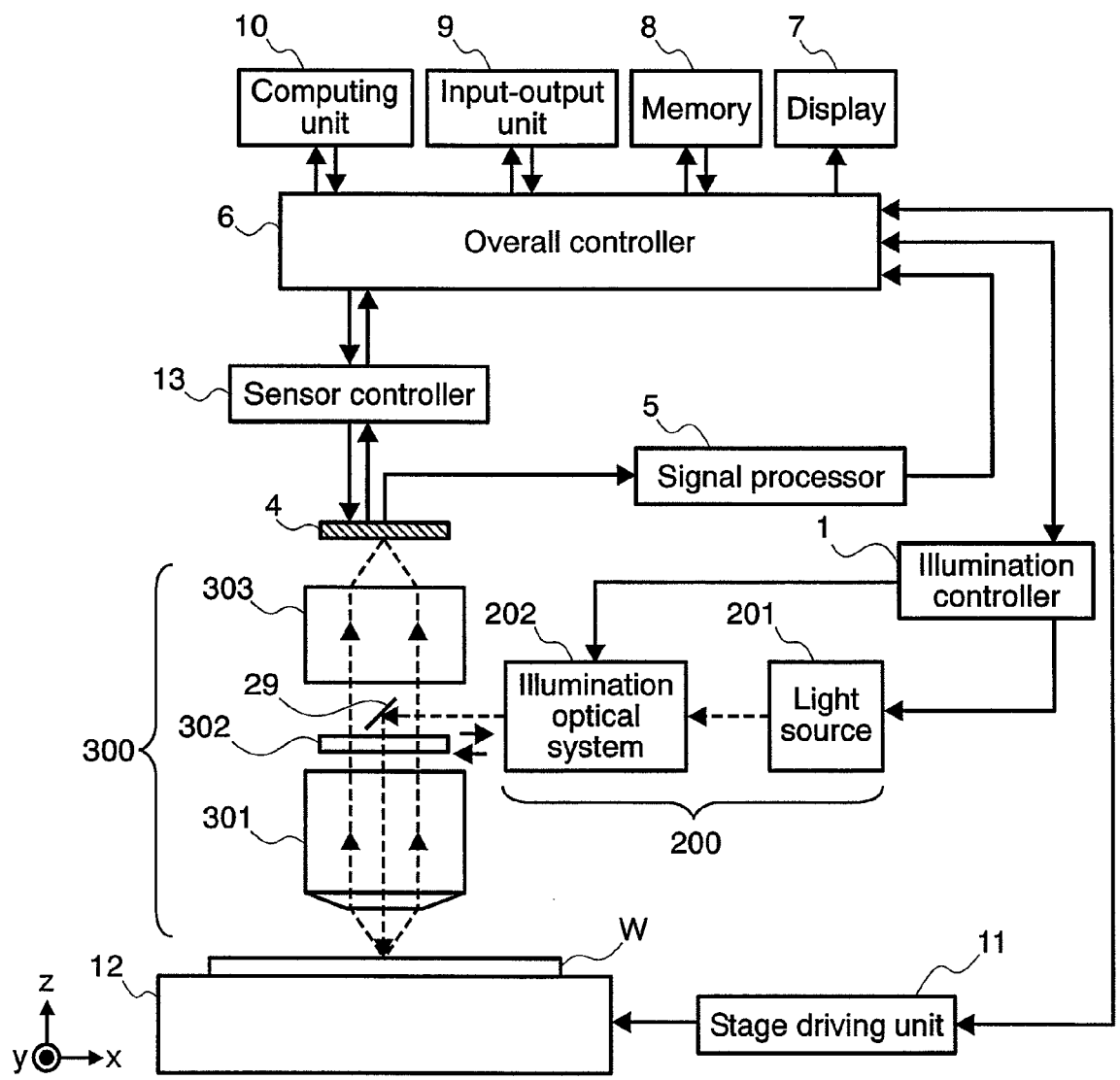
FIG. 13 is a schematic diagram to explain a second modification of the embodiment of FIG. 1.
Figure 14:
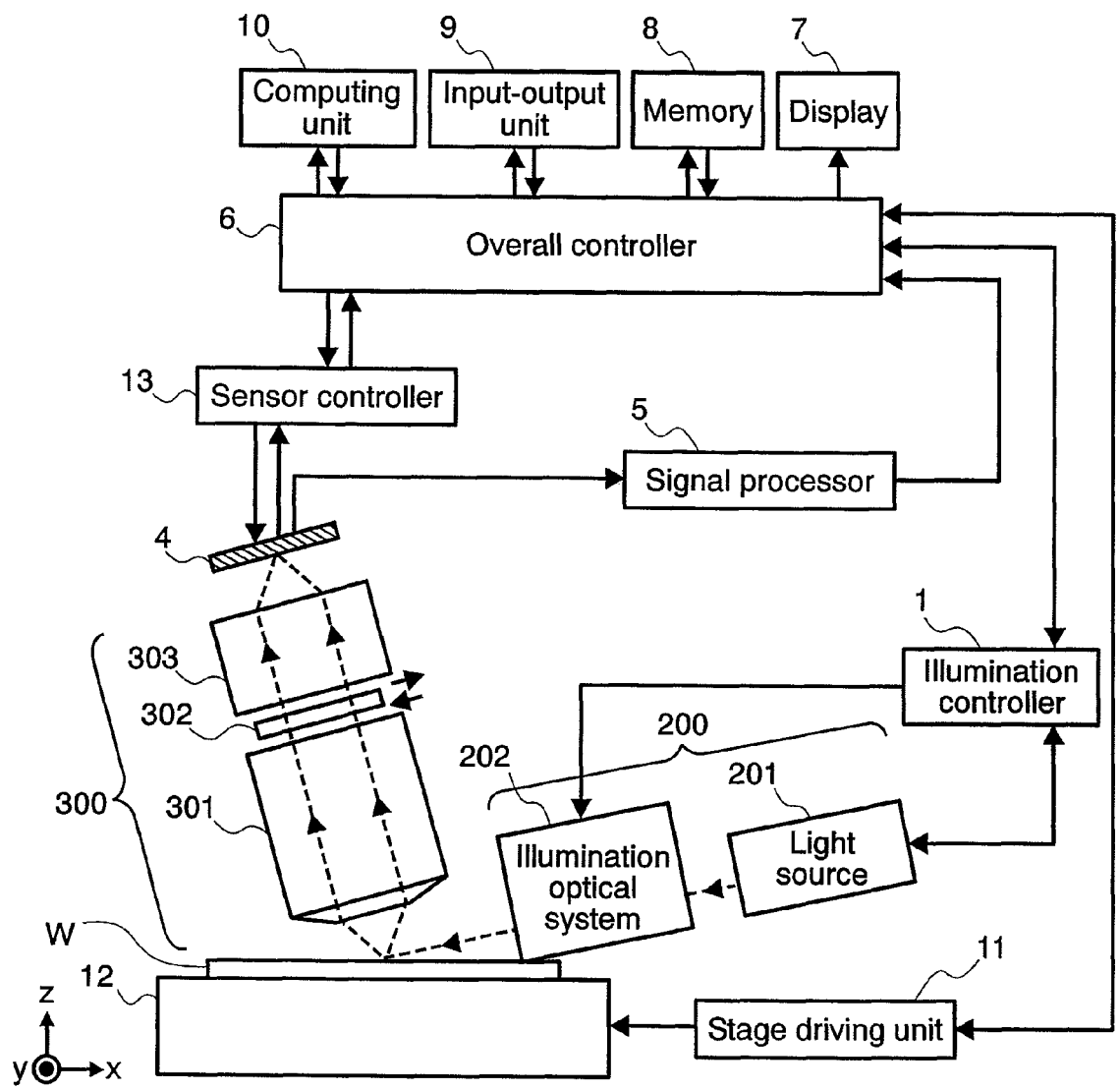
FIG. 14 is a schematic diagram to explain a third modification of the embodiment of FIG. 1.

FIGS. 12, 13, and 14 show modifications of the first embodiment.

FIG. 12 shows a first modification. It is different from the example shown in FIG. 1 in that the illuminating light enters from a plurality of directions or all the directions of the periphery of the objective lens 301. It constitutes a darkfield optical system where a zero-order light (specular reflected light) from the subject W does not enter a detection NA. The illumination optical system 200 comprises a light-guiding means 28 guiding light around the objective lens comprised of a flux of optical fibers, reflection mirrors etc., and a light-collecting means (not shown), such as a paraboloidal mirror etc. provided around the objective lens, collecting the illuminating light guided around the objective lens onto the subject W. The noise during the comparison of the neighboring chips is reduced by illuminating the subject W from all directions and by making the difference in the pattern's random way of reflecting light depending on the azimuth angle of illumination even and stabilizing it.

FIG. 13 shows a second modification, which is different from the example shown in FIG. 1 in that incident illuminating light enters the subject W by using a beam splitter 29. A brightfield optical system is constructed where the zero-order light (specular reflection light) from the subject W enters the detection NA. As a beam splitter 29, for example, a polarization beam splitter is used. Since the zero-order light (specular reflection light) enters the detection optical system, the difference in reflectance caused by the material of the pattern is observed as a contrast, which is suitable for inspecting the defects of the shape of the pattern. According to the material or the shape of the pattern, there may be a considerable difference in the detected amount of light between the bright portion (a region where relatively large amount of light is detected) and a dark portion (a region where relatively small amount of light is detected) within a field of view of the detection optical system 300, and there may take place saturation of the electron multiplying CCD sensor 4 in the bright portion or a shortage of amount of light in the dark portion. In such a case, with the spatial filter 302, by selecting attenuating/shading the diffracted light of a given order or a scattered light emitted at a given scattering angle, and by adjusting and decrease the difference in the amount of light between the bright portion and the dark portion, it becomes possible to inspect both the bright portion and dark portion at the same time and to secure the region to be inspected.

FIG. 14 shows a third modification, which is different from the example shown in FIG. 1 in that the angle formed between the detection direction of the detection optical system 300 and the surface of the subject W is not 90°, namely oblique detection is conducted. As shown in FIG. 15A, the direction of the detection in the third modification is shown by using an azimuth angle $\theta$ and an elevation angle $\phi$ while using the illumination direction (in FIG. 15, the direction in which X extends from positive to negative in the X-Y plane) as a reference.

Now, how to select the detection direction, namely, the azimuth angle $\theta$ and elevation angle $\phi$ in the third modification will be described. As an angle peculiar to the illumination direction, when detecting side scattering from the pattern or foreign matters/defects, the azimuth angle $\phi$ of around ±90° is preferred. When detecting forward scattering, the azimuth angle $\phi$ of around 180° is preferred. Further, when detecting backward scattering, the azimuth angle $\phi$ of around 0° is preferred. Further, when detecting a pattern having two directionality perpendicular to each other, it is possible to inspect the portions of having respective directionality completely by detecting the area around an azimuth angle $\phi$ of 45° or 135°.

As an elevation angle $\phi$, when a transparent film is formed on the subject pattern to be inspected, for example, an angle may be selected such that the variation in the intensity of the scattered light caused by the film thickness interference becomes small. For example, as a relatively small elevation angle, the elevation angle $\phi$ between 10° and 450 may be selected.

As a method to select the detection direction in the third modification, one of the selection examples of the above azimuth angles $\phi$ and one of the selection examples of the above elevation angles $\psi$ may be combined. As specific examples, FIGS. 15B and 15C show that ($\phi$, $\psi$)=(90°, 30°) and (135°, 45°), respectively.

Also, two different detection directions may be selected from among the detection directions in the third modification and detection optical systems may be provided in respective directions. Alternatively, detection optical systems may be provided in the detection direction of FIG. 1 and the detection direction of the third modification, respectively. In this regard, electron multiplying CCD sensors may be provided in both the two detection optical systems. Alternatively, an electron multiplying CCD sensor may be provided in one of the two detection optical systems and a CCD sensor which does not multiply electrons may be provided in the other detection optical system. In the latter case, high sensitivity of the electron multiplying CCD sensor can be effectively used by providing the electron multiplying CCD sensor in the detection direction of the two detection directions where the intensity of detection light is relatively small in relation to the illuminating direction.

Figure 16:
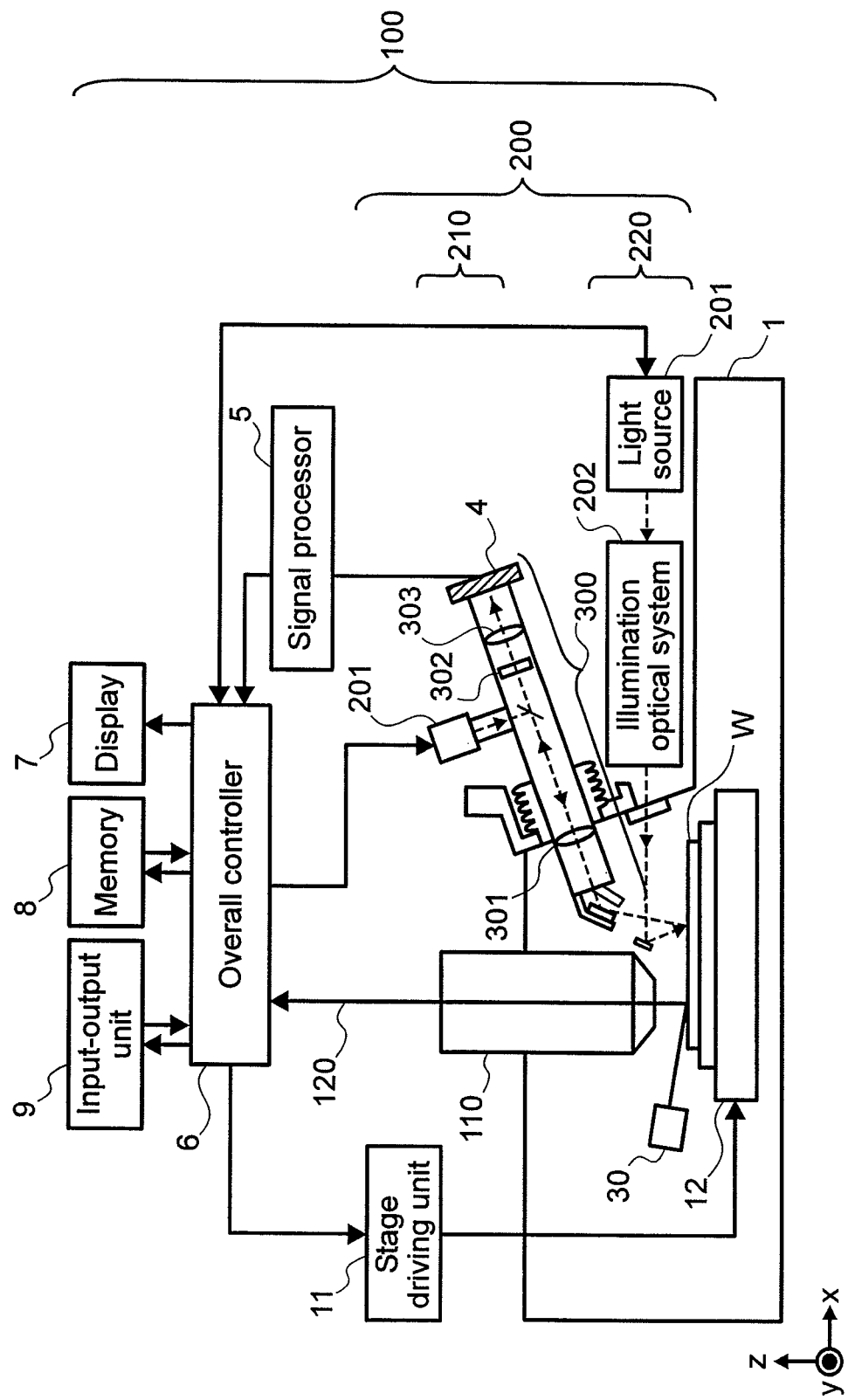
FIG. 16 is a schematic diagram to explain a fourth modification of the embodiment of FIG. 1.

As a fourth modification, FIG. 16 shows an example in which a photo-detector portion of the detection optical system of the defect inspection device having an electronic microscope is replaced with an electron multiplying CCD sensor. The defect inspection device comprises a memory 8, a defect observing means 100, a stage 12, and an electronic microscope 110. In the memory 8, information about the position of the defect obtained by detecting in advance the subject W on which patterns are formed with another inspection device is stored. The defect observing means 100 includes an illumination system 200 illuminating defects and a detection optical system 300 detecting the illuminated defects. The stage 12 on which the subject W is placed puts a defect to be observed within the view field of the detection optical system 300 according to the position information of the defect stored in the memory 8. The electronic microscope 110 observes the defect detected by the defect observing means 100.

According to this construction, the illumination system 200 comprises a first illuminating unit 210 illuminating the subject W at a large incident angle and a second illuminating unit 220 illuminating the subject W at a small incident angle. Based on the position information, stored in the memory, of the defect detected in advance by using another inspection device, the illumination system 200 places the defect to be observed within a view field of the detection optical system 300 of the defect observing means 100. Further, the illumination system 200 illuminates the defect placed in the view field and detects it by using the detection optical system 300, and the detected defect is observed by the electronic microscope 110.

The electronic microscope (SEM) 110 is a device which irradiates the subject W with electron beams, scans it, detects secondary electrons generated from the subject W, and to observe the image with a high magnification. Defect map data, which is the position information of the defect on the subject W outputted by the other inspection device, is inputted through the input-output unit 9 (including a keyboard, a network, a removable medium, etc.). With respect to an electron beam axis 120 of the electronic microscope (SEM) 110, the XY stage 12 is moved to the position substantially matching in the XY direction. The position in the Z direction on the subject W is detected by a focus detection system 30 (in FIG. 16, the light emitting side is shown and the light receiving side is omitted). Thus, the defect on the subject W detected is observed while controlling the focus of the electron beam by the overall controller 6 so that the SEM image is clear.

Further, a secondary electron detector (not shown) comprises a photoelectric converter, an EDX, etc. provided so as to face a point where the electron beam axis 120 and the subject W cross with each other. With the above construction, by using the electronic multiplying CCD sensor 4 as a photo-detector of the detection optical system 300, foreign matters/defects smaller than the ones detected by a conventional method can be detected and observed with high sensitivity and at high speed.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A defect inspection device, comprising:
an illumination system for obliquely irradiating a subject on which a pattern is formed with light;
a detection optical system for focusing light at least one of reflected and scattered from said subject which is irradiated with light by the illumination system, and for detecting the focused light at least one of reflected and scattered as images; and
a signal processor arranged to compare the images by the detection optical system and to detect at least one of foreign matters and defects on said subject based on signals detected by the detection optical system,
wherein said detection optical system comprises an object, a tube lens and a plurality of solid image pick-up devices having different detection sensitivity to detect light at least one of reflected and scattered from said subject, and
wherein the object lens and the tube lens are configured to focus the reflected and scattered light on the plurality of solid image pick-up devices.

2. A defect detecting device according to claim 1,
wherein one of said plurality of solid image pick-up devices having different detection sensitivity is an electron multiplying solid image pick-up device capable of multiplying electrons generated through photoelectric conversion when said at least one of reflected and scattered light is received; and
wherein an electron image multiplication factor at which said electrons are multiplied is variable.

3. A defect detecting device according to claim 2,
wherein said electron multiplying solid image pick-up device multiplies electrons generated through photoelectric conversion by causing electron-bombard multiplication when said at least one of reflected and scattered light is received; and
wherein an electron multiplication factor is made variable by controlling applied voltage of said electron bombardment.

4. A defect detecting device according to claim 2,
wherein said electron multiplying solid image pick-up device multiplies electrons generated through photoelectric conversion by causing impact ionization when said at least one of reflected and scattered light is received; and
wherein an electron multiplication factor is made variable by controlling transfer voltage of an electron multiplying unit causing said impact ionization.

5. A defect detecting device according to claim 2, wherein said electron multiplying solid image pick-up device has an anti-blooming characteristic.

6. A defect detecting device according to claim 2, wherein said electron multiplying solid image pick-up device outputs a plurality of detected signals in parallel.

7. A defect detecting device according to claim 1,
wherein said illumination system irradiates said subject obliquely with light longitudinal in one direction; and
wherein said detection optical system has a spatial filter selectively shading or attenuating diffracted light from the pattern of the subject irradiated with said light longitudinal in one direction.

8. A defect detecting device according to claim 1,
wherein said detection optical system comprises an optical path branching means and a plurality of solid image pick-up devices having different detection sensitivity to detect light at least one of reflected and scattered from the subject and branched by the optical path branching means.

9. A defect detecting device according to claim 1,
wherein the detection optical system detecting the focused light at least one of reflected and scattered as images from the same region of the subject.

10. A defect inspecting method comprising the steps of:
irradiating a subject on which a pattern is formed with light emitted from a light source through an illumination optical system;
focusing light at least one of reflected and scattered from said subject by the irradiation through a detection optical system with an object lens, a tube lens, and a plurality of solid image pick-up devices, detecting the focused light at least one of reflected and scattered as images and converting to electric signals; and
comparing the converted electric signals and detecting at least one of foreign matters and defects on said subject,
wherein the at least one of reflected and scattered light from said subject is branched by an optical path branching means and each of the branched lights are received by different solid image pick-up devices having different detection sensitivity, and
wherein the object lens and the tube lens are configured to focus the reflected and scattered light on the plurality of solid image pick-up devices.

11. A defect detecting method according to claim 10,
wherein one of said plurality of solid image pick-up devices having different sensitivity is an electron multiplying solid image pick-up device which can multiply electrons produced through photoelectric conversion when said at least one of reflected and scattered light is received; and
wherein the electron multiplying solid image pick-up device receives the light while changing an electron multiplication factor based on information about the amount of the at least one of reflected and scattered light from said subject.

12. A defect detecting method according to claim 10,
wherein said solid image pick-up device outputs the electric signals produced through reception and conversion of said at least one of reflected and scattered light in parallel; and
wherein said solid image pick-up device processes, in parallel, the electric signals outputted in parallel and detects at least one of foreign matters and defects on said subject.

13. A defect detecting method according to claim 10,
wherein the subject on which said pattern is formed is irradiated obliquely with light longitudinal in one direction; and
wherein the diffracted light from the subject irradiated with the light longitudinal in one direction is selectively shaded or attenuated by a spatial filter, and received and detected by said solid image pick-up device.

14. A defect detecting method according to claim 10,
wherein the at least one of reflected an scattered light from said subject by said irradiation is received by the solid image pick-up device having an anti-blooming characteristic and converted into electric signals.

* * * * *